(12) United States Patent
Munro

(10) Patent No.: US 6,683,120 B2
(45) Date of Patent: Jan. 27, 2004

(54) BIOADHESIVE COMPOSITIONS

(75) Inventor: Hugh Semple Munro, Chipping Camden (GB)

(73) Assignee: First Water Limited, Wiltshire (GB)

( * ) Notice: Subject to any disclaimer, the term of this patent is extended or adjusted under 35 U.S.C. 154(b) by 0 days.

(21) Appl. No.: 09/917,056

(22) Filed: Jul. 27, 2001

(65) Prior Publication Data

US 2002/0026005 A1 Feb. 28, 2002

Related U.S. Application Data

(63) Continuation of application No. PCT/GB00/00304, filed on Feb. 2, 2000.

(51) Int. Cl.$^7$ .......................... C08L 15/00; A61L 15/16
(52) U.S. Cl. ............... 523/111; 424/448; 428/355 RA; 524/322; 524/277; 524/481; 524/514; 524/578; 525/57; 525/58; 525/59; 525/61
(58) Field of Search .................. 524/270, 277, 524/322, 481, 505, 578, 95, 514; 523/111; 428/355 RA; 525/57, 58, 59, 61; 424/448

(56) References Cited

U.S. PATENT DOCUMENTS

| 5,173,302 A | | 12/1992 | Holmblad et al. | |
|---|---|---|---|---|
| 5,234,992 A | * | 8/1993 | Gyory et al. | ................. 524/47 |
| 5,573,778 A | * | 11/1996 | Therriault et al. | .......... 424/448 |
| 5,670,557 A | | 9/1997 | Dietz et al. | |

FOREIGN PATENT DOCUMENTS

| EP | 0012402 | 6/1979 |
|---|---|---|
| EP | 0 676 457 A1 | 10/1995 |
| EP | 0 855 190 A1 | 7/1998 |
| WO | WO 00/06214 | 2/2000 |

OTHER PUBLICATIONS

Vamvakaki, et al., *Polymer*, 39 (11): 2331–2337 (1998).

* cited by examiner

*Primary Examiner*—Tatyana Zalukaeva
(74) *Attorney, Agent, or Firm*—Nixon Peabody LLP

(57) ABSTRACT

A bioadhesive composition for use as a skin adhesive, the composition formed by polymerizing with cross-linking and/or entanglement an aqueous reaction mixture comprising effective amounts of at least one monomer dissolved or suspended therein and capable of forming a hydrogel on polymerization, optionally at least one cross-linking agent for the monomer, and water, said composition having an elastic modulus (G') and a viscous modulus (G"), wherein the degree of polymerization and/or the degree of cross-linking and/or entanglement are selected to control the skin adhesion properties of the bioadhesive composition having regard to the rate of change of tan delta (G"÷G') against frequency in a diagnostic portion of the frequency range 0.01 to 300 rad/s, typically the lower end of the said frequency range below about 100 rad/s.

90 Claims, 9 Drawing Sheets

BIOADHESIVE COMPOSITIONS

This application is a continuation of copending international application PCT/GB00/00304, filed Feb. 2, 2000, which is hereby incorporated by reference, which claims benefit of G.B. application 9902238.6, filed Feb. 2, 1999.

FIELD OF THE INVENTION

The present invention relates to bioadhesive compositions. One possible application of the compositions of the invention is as skin adhesives in the field of biomedical skin electrodes. These electrodes incorporate bioadhesive compositions which are electrically conductive. Another possible application of the compositions of the invention is as skin adhesives particularly in the field of medical skin coverings, particularly wound dressings.

BACKGROUND OF THE INVENTION

Biomedical skin electrodes are widely used in a variety of situations, whenever for example it is required to establish an electrical connection between the surface of the body of a patient and external medical equipment for transmission of electrical signals.

Modern medicine uses many medical procedures where electrical signals or current are received from or delivered to a patient's body. The interface between medical equipment used in these procedures and the skin of the patient is usually some sort of biomedical electrode. Such electrodes typically include a conductor which must be connected electrically to the equipment, and a conductive medium adhered to or otherwise contacting the skin of the patient, and they are of varying types with a wide variety of design configurations which will generally depend on their intended use and whether for example they are to be used as transmission electrodes or sensing i.e. monitoring electrodes.

Among the therapeutic procedures using biomedical electrodes are transcutaneous electric nerve stimulation (TENS) devices used for pain management; neuromuscular stimulation (NMS) used for treating conditions such as scoliosis; defibrillation electrodes to dispense electrical energy to a chest cavity of a mammalian patient to defibrillate heart beats of the patient; and dispersive electrodes to receive electrical energy dispensed into an incision made during electrosurgery.

Among diagnostic procedures using biomedical electrodes are monitors of electrical output from body functions, such as electrocargiograms (ECG) for monitoring heart activity and for diagnosing heart abnormalities.

For each diagnostic, therapeutic, or electrosurgical procedure, at least one biomedical electrode having an ionically conductive medium containing an electrolyte is adhered to or is otherwise contacted with mammalian skin at a location of interest and is also electrically connected to electrical diagnostic, therapeutic, or electrosurgical equipment A critical component of the biomedical electrode is the conductive medium which serves as the interface between the mammalian skin and the diagnostic, therapeutic, or electrosurgical equipment, and which is usually an ionically conductive medium.

Biomedical electrodes are used among other purposes to monitor and diagnose a patient's cardiovascular activity. Diagnostic electrodes are used to monitor the patient immediately and are only applied to the patient for about five to ten minutes. Monitoring electrodes, however, are used on patients in intensive care for up to three days continuously. In contrast, Holter electrodes are used to monitor a patient during strenuous and daily activities.

Although all of the biomedical electrodes just referred to are used to record cardiovascular activity, each electrode requires specific features or characteristics to be successful. Thus, the diagnostic electrode does not have to remain adhered to a patient for extensive periods but it does have to adhere to hairy, oily, dry and wet skin effectively for the five to ten minutes of use. The monitoring electrode has to adhere for a longer period of time although the patient is often immobile during the monitoring period The Holter electrode is susceptible to disruption from adhesion due to physical motion, perspiration, water, etc., and therefore requires the best adhesion and at the same time comfort and electrical performance.

In the biomedical electrodes known in the prior art the ionically conductive medium which serves as an interface, between the skin of a mammalian patient and the electrical instrumentation, ranges from conductive gels and creams to conductive pressure sensitive adhesives. However, while the conductive media can be in the form of pressure sensitive conductive adhesives, for monitoring or Holter biomedical electrodes the use of such conductive adhesives is not generally adequate on their own to maintain adhesion to mammalian skin and additional hypoallergenic and hydrophobic pressure sensitive adhesives may be employed around the conductive medium to provide the required mammalian skin adhesion. U.S. Pat. No. 5,012,810 (Strand et al.) and U.S. Pat. Nos. 4,527,087, 4,539,996, 4,554,924 and 4,848,353 (all Engel), the disclosures of which are incorporated herein by reference, are examples of documents that disclose biomedical electrodes which have a hydrophobic pressure sensitive adhesive surrounding the conductive medium.

In general, a desirable skin electrode is one which maintains good electrical contact with the skin and is free of localised current hot spots, i.e. exhibits uniform conductivity. For example, it has been found that a prior art electrode utilising karaya-gum tends to creep in use and flatten out, exposing skin to possible direct contact with the current distribution member or lead wire. A desirable skin electrode should also usually have a low electrical impedance.

As mentioned above, another possible application of the compositions of the invention is in the field of medical skin coverings, for example medical tapes, wound dressings and bandages, and most particularly wound dressings. In general, a desirable wound dressing bioadhesive composition maintains good adhesion to skin of varying moisture levels, while maintaining the dressing in position on the skin and permitting moisture and skin exudates to be transmitted away from the skin. The bioadhesive composition may suitably incorporate an antimicrobial agent, to reduce the possibility of infection of the wound. U.S. Pat. No. 5,670, 557 (Dietz et al) and the prior art referred to therein, the disclosures of which are incorporated herein by reference, are examples of documents that disclose wound dressings which have a pressure sensitive adhesive which maintains the wound dressing in position on the skin.

EP-A-0850625 and EP-A-0850649 (The Procter & Gamble Company), the disclosures of which are incorporated herein by reference, describe a topical adhesive for application of functional articles to the skin, the functional articles being cosmetic or pharmaceutical delivery articles, decorative or cleaning articles (EP-A-0850649) or disposable absorbent articles (EP-A-0850625). The adhesive has particular selected rheological properties, which are expressed in part by using the difference between the elastic modulus and the viscous modulus at two fixed frequencies of applied stress, namely 1 rad/sec and 100 rad/sec.

SUMMARY OF THE INVENTION

It is an object of this invention to provide hydrogel skin adhesives possessing controlled and predictable adhesive properties which may be readily varied to suit different uses and, in the case of medical electrodes, wound dressings or similar devices, different configurations or applications.

Adhesives used for skin contact applications need to exhibit both good levels of adhesion and pain free removal. The adhesive must be skin compatible and not be harsh or aggressive towards the skin or cause skin irritation or inflammation.

The problem of achieving the desired level of adhesion is exacerbated under wet conditions. Conventional bioadhesives generally provide poor adhesion to wet skin, such adhesion generally reducing as water is absorbed by the bioadhesive. It is hence very important that the adhesive is also stable to exposure to excess quantities of liquid, such as water and in some applications in particular to urine or blood, so that it will not lose its adhesive strength on exposure to water.

Individual aspects of the invention aim, respectively, to provide hydrogel skin adhesives which provide good adhesion to moist and wet skin and such adhesives for use in biomedical skin electrodes or wound dressings. These hydrogels would be useful for adhesion to skin which is subject to flushing by water or aqueous solutions. In such circumstances there is a need for materials capable of adhering to skin that can maintain or increase their adhesion on water up-take.

Thus the present invention seeks in one aspect to provide a bioadhesive which adheres to wet skin, is stable and maintains its adhesiveness even when exposed to excessive amounts of liquid.

Other aspects of the present invention aim to control and adjust the extent to which the bioadhesive maintains or loses its adhesiveness on exposure to liquid.

Examinations of the rheological properties of adhesives have been successfully used to characterise and differentiate adhesive behaviour. See, for example, "Viscoelastic Properties of Pressure Sensitive Adhesives" in The Handbook of Pressure Sensitive Adhesives (ed. D. Satas) pages 158 to 203 (1989). Typically, the elastic modulus (G') and the viscous modulus (G") are measured in a controlled stress rheometer, e.g. a parallel plate rheometer using a film sample of the bioadhesive composition between the plates, over a frequency range of 0.01–300 rad/s at a given temperature. For skin applications the appropriate temperature is 37° C. The moduli at low frequencies relate to the initial bonding of the adhesive to skin and the moduli at higher frequencies to de-bonding. For conventional prior art hydrogel adhesives both G' and G" increase within increasing frequency. On absorption of water these trends are maintained but the absolute values of the moduli decrease. The ratio of G" to G' (G"÷G') is referred to as tan delta. This gives an indication of the balance of contribution arising from the viscous and elastic properties of the material. It is found that many conventional hydrogel based adhesives, on taking up water in an amount that exceeds 3% by weight of the as made bioadhesive, lose their adhesive properties. For such compositions tan delta tends to increase with increasing frequency. In some cases the curve of tan delta plotted against frequency may show a point of inflexion or a maximum at relatively high frequencies, i.e. the rate of change of the tan delta curve may be zero at one or more point. However the general trend is that tan delta increases at low frequencies with increasing frequency. High values of tan delta at high frequency indicate an increasing contribution to the de-bonding process associated with the viscous component of the gel.

We have found that the behaviour of tan delta, when plotted against frequency over a portion (typically the very low frequency end) of the normal frequency range 0.01–300 rad/s at 37° C. is diagnostic of many of the skin adhesion properties found in the bioadhesive composition.

Moreover, we have found that the behaviour of tan delta, when plotted against frequency at these diagnostic frequencies, can be manipulated by adjustment of the amounts of certain components of the aqueous reaction mixture and by control of the polymerisation conditions, with the result that, for the first time, the skin adhesion properties of bioadhesive compositions can be controlled to a relatively high degree of accuracy, compared with the accuracy available hitherto.

According to a first aspect of the present invention, there is provided a bioadhesive composition for use as a skin adhesive, the composition formed by polymerising with cross-linking and/or entanglement an aqueous reaction mixture comprising at least one monomer dissolved or suspended therein and capable of forming a hydrogel on polymerisation, optionally at least one cross-linking agent for the monomer, and water, said composition having an elastic modulus (G') and a viscous modulus (G"), wherein the degree of polymerisation and/or the degree of cross-linking and/or entanglement, are selected to control the skin adhesion properties of the bioadhesive composition having regard to the rate of change of tan delta (G"÷G') against frequency in a diagnostic portion of the frequency range 0.01 to 300 rad/s.

The selection of the degree of polymerisation and/or the degree of cross-linking and/or entanglement in the polymerised composition is suitably achieved by selection of the amount of monomer in the aqueous reaction mixture, the amount of any cross-linking agent present in the aqueous reaction mixture, and/or the reaction conditions for the polymerisation with cross-linking and/or entanglement. This selection is within the abilities of one skilled in this art, the control parameters being discussed in more detail below.

The monomer may, for example, be at least one hydrophilic monomer, or a mixture of at least one hydrophilic monomer with at least one hydrophobic monomer.

The bioadhesive composition may be used as a skin adhesive in a biomedical skin electrode or in a wound dressing. These uses of the bioadhesive composition are novel and constitute a second aspect of the present invention.

According to a third aspect of the present invention, there is provided a method for preparing a bioadhesive composition for use as a skin adhesive, the method comprising:

(a) forming an aqueous reaction mixture comprising at least one monomer dissolved or suspended therein and capable of forming a hydrogel on polymerisation, optionally at least one cross-linking agent for the monomer, and water; and (b) polymerising with cross-linking and/or entanglement the aqueous reaction mixture, wherein the degree of polymerisation and/or the degree of cross-linking and/or entanglement, are selected to control the skin adhesion properties of the bioadhesive composition having regard to the rate of change of tan delta (G"÷G') against frequency in a diagnostic portion of the frequency range 0.01 to 300 rad/s, where G" is the viscous modulus of the bioadhesive composition and G' is the elastic modulus of the bioadhesive composition.

According to a fourth aspect of the present invention, there is provided a method for controlling the skin adhesion properties of a bioadhesive composition for use as a skin adhesive, the method comprising polymerising with cross-linking and/or entanglement an aqueous reaction mixture comprising at least one monomer dissolved or suspended therein and capable of forming a hydrogel on polymerisation, optionally at least one cross-linking agent for the monomer, and water; wherein the reaction is conducted so that the degree of polymerisation and/or the degree of cross-linking and/or entanglement is selected to control the skin adhesion properties of the bioadhesive composition having regard to the rate of change of tan delta (G"÷G') against frequency in a diagnostic portion of the frequency range 0.01 to 300 rad/s, where G" is the viscous modulus of the bioadhesive composition and G' is the elastic modulus of the bioadhesive composition.

The measurement of elastic modulus and viscous modulus is carried out using a controlled stress rheometer at an appropriate temperature for the intended use of the bioadhesive (e.g. about 37° C.) The controlled stress rheometer may suitably be a parallel plate rheometer, suitably testing a film of the bioadhesive composition between the parallel plates. Normally, the diagnostic effect of the rate of change of tan delta is best observed on the "as made" hydrogel before substantial uptake of water.

The expression "dissolved" as used herein includes all forms of dissolution and intimate monophasic admixture. The expression "suspended" as used herein includes all forms of intimate non-monophasic admixture, for example emulsification, including microemulsification.

The expression "diagnostic portion of the frequency range 0.01 to 300 rad/s" as used herein refers to that portion of the frequency range in which the rate of change of tan delta against frequency can be substantially reproducibly altered by control of the parameters stated herein and in which the said rate of change of tan delta correlates with skin adhesion properties of the bioadhesive composition.

It has been found, in particular, that bioadhesive compositions having useful adhesive responses to water uptake may exhibit a zero rate of change of tan delta against frequency at only one point in the frequency range 0.01 to 300 rad/s. Typically, the diagnostic portion of the frequency range 0.01 to 300 rad/s will be the portion below the frequency at which the zero point is observed.

This one point in the frequency range 0.01 to 300 rad/s may, for example, be a maximum or a minimum. When it is a maximum, a so-called "water unstable" bioadhesive composition is typically present. For further details of such compositions, reference is made to our International (PCT) Patent Application No. PCT/GB99/02524, the disclosure of which is incorporated herein by reference. When the point is a minimum, a so-called "water stable" bioadhesive composition is typically present. For further details of such compositions, reference is made to our International (PCT) Patent Application No. PCT/GB99/02505, the disclosure of which is incorporated herein by reference.

For the purposes of the present invention "water-stability" will be defined as the maintenance of adhesion to skin or another substrate from a level of about 80% to more than 100% of the initial value of the hydrogel adhesive, after the water content of the hydrogel has increased by absorption of water from the environment external to the hydrogel. The amount of water absorbed may typically be from about 3% to about 30% of the weight of the "as made" hydrogel. Correspondingly, "water-instability" will be defined as the reduction of adhesion to skin or another substrate to below about 80% of the initial value of the hydrogel adhesive, after the water content of the hydrogel has increased by absorption of water from the environment external to the hydrogel.

DETAILED DESCRIPTION OF THE INVENTION

The skin adhesion properties to be controlled include initial adhesive strength, long-term adhesive strength, peel strength, wet skin performance, greasy skin performance, hair adhesion, residual adhesive amount after removal and cohesive strength.

The rate of change of tan delta against frequency, within the frequency range 0.01 to 300 rad/s or a diagnostic portion thereof, can be varied according to the invention within a range of negative values, between positive and zero, between negative and zero, or around zero. The zero value may be a continuous zero or a point zero. These variations will typically directly affect the adhesive properties of the composition, most particularly the extent of maintenance or loss of adhesiveness in the presence of varying amounts of water or other liquids.

The diagnostic portion of the frequency range 0.01 to 300 rad/s is typically the low-frequency end of the range, suitably below about 100 rad/s, more suitably below about 30 rad/s and most suitably below about 10 rad/s. At this low frequency end of the range, a positive rate of change of tan delta with increasing frequency (i.e. an increasing tan delta with increasing frequency) is found in many cases to be diagnostic of water instability, and a negative or approximately zero rate of change of tan delta with increasing frequency (i.e. a decreasing tan delta within increasing frequency) is found in many cases to be diagnostic of water-stability.

It should be noted that the rate of change of tan delta is not necessarily constant over the diagnostic portion of the frequency range, and some variation is normal. Moreover, the diagnostic portion for one bioadhesive composition will not necessarily be the same as the diagnostic portion for another bioadhesive composition. For this reason, it may be necessary to conduct trials, in order to determine the diagnostic portion of the frequency range for a particular bioadhesive composition. Such trials will be well within the ability of one of ordinary skill in this art.

Particular aspects of the polymerisation with cross-linking and/or entanglement which are susceptible to control according to the invention include:

1. the nature of the monomer(s) (M), in particular it/their reactivity and the number of polymerisable functions per molecule;
2. the nature of any cross-linking agent(s) (XL), in particular it/their reactivity and the number of reactive functions per molecule;
3. the amounts of the monomer(s) in the aqueous reaction mixture;
4. the amount of any cross-linking agent(s) in the aqueous reaction mixture;
5. the presence of any polymerisation inhibitor(s);
6. the presence of any chain transfer agent(s);
7. the weight fraction of monomer(s) and cross-linking agent(s) in the reaction mixture;

8. in the case of an initiated polymerisation (e.g. free radical initiated polymerisation), the initiation efficiency (e.g. in the case of photoinitiation, the incident light intensity, the type of initiator and the incident wavelength distribution);

9. the reaction time;

10. any combination of 1 to 9.

Where a cross-linking agent (XL) is present, the relative amounts of M and XL (i.e. the M:XL ratio) in the aqueous reaction mixture may have a significant effect on the adhesive properties of the bioadhesive composition, and this combination of aspects 3 and 4 above will typically require particular attention.

While the exercise of the control parameters according to the present invention may require a small degree of practice and experiment on the part of the person skilled in the art, this is not an onerous task for such a person. All the control parameters-which are quantitatively monitorable by using the diagnostic tan delta measurements-are potentially reproducible and sufficiently defined to enable a substantially higher degree of control to be exerted on the preparation of bioadhesive hydrogels than has been possible hitherto.

The M:XL molar ratio may suitably be selected within the range of about 10,000:1 to about 200:1. The M:XL molar ratio must necessarily be approximate, because the molecular weight of a number of commercially available cross-linking agents is not well defined.

In any event, the appropriate M:XL ratio may readily be selected after simple experimentation to determine the controlling ratio, given the particular M and XL used and the desired adhesive properties of the composition, by monitoring the rate of change of tan delta in the diagnostic portion of the frequency range 0.01 to 300 rad/s, in accordance with the present invention.

According to one particular form of the invention, as described above, the rate of change of tan delta against frequency may equal zero at only one point in the frequency range 0.01 to 300 rad/s, more particularly in the frequency range 0.01 to 100 rad/s. A plot of the tan delta values against frequency over the specified range for the freshly produced (as made) bioadhesive compositions of the invention may thus show a single (zero gradient) minimum value. The position of the minimum is dependent on the monomer composition, the degree of polymerisation, the degree of cross linking and/or entanglement, and/or the extent of plasticisation. Adhesive hydrogels exhibiting such rheological behaviour exhibit an increase in adhesion on water up-take whilst maintaining pain free removal properties (i.e. "water stability" as defined herein). Without wishing to be bound by theory, the presence of a single (zero gradient) minimum in the tan delta plots may be interpreted as a truncation of the usual relaxation modes in the gel by a mechanism with a finite relaxation time. The minimum may be related to a sol component of the system (sol-non-crosslinked polymer component) such that the viscous relaxation of the sol interrupts the relaxation of the network (cross-linked and/or entangled polymer). In these particular forms of the present invention, the sol characteristic, when coupled to sufficiently large values of G' and G", provides for materials with good adhesive strength capable of exhibiting increased adhesion on water absorption.

Such water stable compositions exhibit surprisingly good adhesion to both dry and moist skin and on subsequent exposure to large amounts of water. In particular, the hydrogels in accordance with the invention generally provide adhesion on dry skin at no less than 0.5 N/cm. The compositions seem to provide good two stage adhesion with a good initial "first stage" adhesion on first contact of the hydrogel with the skin which adhesion increases with time in the "second stage". Whilst providing sufficient adhesion, it is noted that the water stable hydrogel adhesives of the invention allow for pain free removal from the skin.

Water stability is not always desirable. In some cases a certain loss of adhesion on water uptake may be desirable.

According to the present invention, water instability can be obtained by appropriate control of the extent of cross-linking and/or entanglement. For example, at higher cross-linking and/or entanglement levels than required for the water stable compositions, the rate of change of tan delta within the diagnostic portion of the frequency range 0.01 to 300 rad/s can become positive, a condition associated with water instability (substantial loss of adhesion on water uptake). Our co-pending International (PCT Patent Application No. PCT/GB99/02524 describes in more detail certain hydrogels which exhibit water instability at appropriate levels of cross-linking.

The findings that bioadhesive polymers have a diagnostic portion of the frequency range 0.01 to 300 rad/s, particularly less than about 100 rad/s, more particularly less than about 30 rad/s, and most particularly less than about 10 rad/s, in which the rate of change of tan delta against frequency correlates with bioadhesive properties, and moreover that this rate of change of tan delta can be affected, and even changed in its direction, by control of certain parameters of the aqueous reaction mixture and of the polymerisation with cross-linking and/or entanglement, is surprising and unexpected.

Without wishing to be bound by theory, it is believed that the maximum degree of cross-linking and/or entanglement which is compatible with useful skin adhesion properties is reached when a maximum is observed in the loss compliance J", where $$J''=G''/[(G')^2+(G'')^2].$$

When such a maximum is observed in J", it will typically be at a radian frequency of less than about 30 rad/s, most suitably less than about 10 rad/s. This frequency range for the observed J" maximum is believed to determine the diagnostic frequency range for the particular composition under consideration. In this diagnostic portion of the frequency range the gel generally has a relaxation time of sufficient length that the gel does not flow under its own weight, the same property that is a necessary characteristic of certain important applications of bioadhesive compositions, particularly in biomedical electrodes and wound dressings.

The adhesives with which this invention is concerned generally comprise, in addition to a crosslinked and/or entangled polymeric network, an aqueous plasticising medium and, optionally, at least one electrolyte, whilst the materials and processing methods used are normally chosen to provide a suitable balance of adhesive and electrical properties for the desired application. In particular, the type of water and its activity together with the rheological properties of the hydrogels will generally be controlled to produce a balance of pressure sensitive adhesive properties and, when required, electrical properties. One preferred feature of the process used in carrying out the invention is that to achieve the desired adhesive and electrical properties the final amount of water required in the hydrogel is present in the formulation prior to gellation, i.e. no water is removed from the hydrogel after manufacture and less than 10% during manufacture.

The monomer may, for example, be at least one hydrophilic monomer, or a mixture of at least one hydrophilic monomer with at least one hydrophobic monomer.

The hydrophilic monomer, when present, may for example be at least one ionic water-soluble monomer, or at least one non-ionic water-soluble monomer, or a mixture thereof. It is preferred that the aqueous reaction mixture should contain at least one ionic water-soluble monomer.

Where a hydrophobic monomer is present, the aqueous reaction mixture may be homogeneous or may be phase segregated, e.g. as an emulsion or microemulsion. Solubilising and/or emulsifying agents may be used to maintain the hydrophobic material in the desired state of solubilisation or emulsification in the aqueous reaction mixture. Examples of a solubilised system are contained in our co-pending International PCT Patent Application No. PCT/GB00/00302/ WO00/46319 (Attorneys Reference DLB/67115/001) being filed simultaneously with the present application and claiming priority from our European Patent Application No. 99300740.0. The disclosures of the said co-pending International Patent Application and the said European Patent Application are incorporated herein by reference.

The aqueous reaction mixture may suitably include further conventional agents such as at least one photoinitiator, at least one plasticiser or humectant, at least one electrolyte, at least one surfactant or any combination thereof.

The cross-linking agent may, for example, be at least one multi-functional cross-linking agent which is reactive with the monomer(s) present in the aqueous reaction mixture.

Particular examples of the components which may be present in the aqueous mixture will now be given.

Monomers

According to the present invention a 3-dimensional matrix, also referred to herein as a hydrogel, comprises a polymer which is cross-inked and/or entangled to the required degree. The polymer includes repeating units derived, for example, from vinyl alcohols, vinyl ethers, carboxy vinyl monomers, vinyl ester monomers, esters of carboxy vinyl monomers, vinyl amide monomers, anionic vinyl monomers, hydroxy vinyl monomers, cationic vinyl monomers containing amine or quaternary groups, N-vinyl lactam monomers, such as N-vinyl pyrrolidone, urethanes, acrylics such as (meth)acrylic acid and its alkali metal (e.g. Na, Li, K) or ammonium salts, (meth)acrylic acid ester derivatives (e.g. acrylic esters such as methyl, ethyl and butyl acrylates, 3-sulphopropyl acrylate alkali metal (e.g. Na, Li, K) or ammonium salts, polyethylene glycol (meth) acrylates, polyethylene glycol alkyl ether acrylate, 2-hydroxyethyl methacrylate, methoxydiethoxyethyl methacrylate or hydroxydiethoxyethyl methacrylate), acrylamides, mono- and di-N-substituted acrylamides (e.g. N,N-dimethylacrylamide, diacetone acrylamide or acryloyl morpholine), acrylonitrile, methacrylamides, sulphonated monomers such as acrylamide sulphonated monomers, for example 2-acrylamido-methylpropane sulphonic acid and its salts (e.g. Na or K salts), and acrylic (3-sulphopropyl) ester, and mixtures of all the foregoing, provided that the monomer or mixture is capable of forming a hydrogel on polymerisation.

For avoidance of doubt, the expression "polymer" and related expressions herein includes homopolymers and copolymers. The term "polymerise" is understood accordingly.

As another alternative, the polymers may be block copolymer thermoplastic elastomers such as ABA block copolymers such as styrene-olefin-styrene block copolymers or ethylene-propylene block copolymers. More preferably such polymers include hydrogenated grade styrol/ethylene-butylene/styrol (SEBS), styrene/isoprene/styrene (SIS), and styrol/ethylene-propylene/styrol (SEPS).

Particularly preferred monomers are acrylics, sulphonated monomers such as sulphonated acrylamides, mono- or di-N-alkylated acrylamides, vinyl alcohols, N-vinyl pyrrolidone and mixtures thereof.

In a preferred embodiment of the invention the monomer comprises a water soluble ionic acrylate based monomer selected for its ability to polymerise rapidly in water. Most preferably the ionic monomer comprises at least one of 2-acrylamido-2-methylpropane sulphonic acid or a substituted analogue thereof or one of its salts, for example, an alkali metal salt such as sodium, potassium or lithium salt. A particularly preferred example of the ionic monomer is 2-acrylamide-2-methylpropane sulphonic acid, commonly known as NaAMPS, available commercially at present from Lubrizol as either a 50% aqueous solution (reference code LZ 2405) or a 58% aqueous solution (reference code LZ 2045A). The above referenced preferred ionic monomer and other suitable ionic monomers may optionally be used in combination with a polymerisable sulphonate or a salt, e.g. an alkali metal salt, such as a sodium, potassium or lithium salt of acrylic (3-sulphopropyl) ester, commonly known as SPA. SPA (e.g. as potassium salt) is available commonly in the form of a pure solid from Raschig. The reaction mixture preferably comprises from about 5% to about 50%, preferably from about 10% to about 50%, and ideally from about 30% to about 50%, by weight of the reaction mixture, of the ionic monomer.

In a further embodiment of the invention any nonionic water soluble monomer present may comprise any of the following either alone or in combination: at least one acrylamide, at least one mono- or di-N-alkylated acrylamide or an analogue thereof and at least one vinyl lactam. Preferably the nonionic water soluble monomer comprises at least one of a di-N-alkylacrylamide or an analogue thereof. The term "analogue" in this context refers to non ionic water soluble monomers containing an alkyl or substituted alkyl group linked to a carbon—carbon double bond via an amido or alkylamido (—CO.NH— or —CO.NR—) function. Examples of such analogues include diacetone acrylamide (N-1,1-dimethyl-3-oxobutyl-acrylamide), N-alkylated acrylamides, N,N-dialkylated acrylamides, N-vinyl pyrrolidone and acryloyl morpholine. N,N-dimethylacrylamide (NNDMA) and/or an analogue thereof is preferred. The reaction mixture preferably comprises from about 10% to about 50%, preferably from about 15% to about 30% and ideally from about 15% to about 25%, by weight of the reaction mixture, of any nonionic water soluble monomer.

The ratio of the ionic monomer to the nonionic monomer is preferably in the range from 30:1 to 1:10.

The total monomer content is ideally in the range from 10% to 70% by weight of the reaction mixture.

In one particularly preferred form of the invention, the monomer may comprise a mixture of at least one ionic water soluble monomer and at least one nonionic water soluble monomer. The ionic water soluble monomer may, for example, comprise 2-acrylamido-2-methylpropane sulphonic acid or a substituted analogue therefor one of its salts, optionally in admixture with SPA or one of its salts, and the nonionic water soluble monomer may, for example, comprise NNDMA. Where the ionic water soluble monomer comprises a mixture of NaAMPS and SPA or one of its salts, it is generally preferred that a high ratio of NaAMPS to SPA, for example 70:30 and above, is used. Copolymers of such a monomer mixture with a suitable nonionic water soluble monomer, such as NNDMA, exhibit the required rheology. For further details of such bioadhesive compositions for use as skin adhesives, refer to our co-pending International (PCT) Patent Application No. PCT/GB00/00302/WO00/46319 (Attorneys Reference DLB/67115/001) and European Patent Application No. 99300740.0, from which it claims priority.

Plasticisers/Humectants

According to a preferred feature of the present invention the 3-dimensional adhesive matrix also comprises a plasticiser or humectant, which is preferably a liquid at room temperature. This material is selected such that the polymer may be solubilised or dispersed within the plasticiser. For embodiments wherein irradiation cross linking is to be carried out, the plasticiser must also be irradiation cross linking compatible such that it does not inhibit the irradiation cross linking process of the polymer. The plasticiser may be hydrophilic or hydrophobic.

Suitable plasticisers include water, alcohols, polyhydric alcohols such as glycerol and sorbitol, and glycols and ether glycols such as mono- or diethers of polyalkylene glycol, mono- or diesterpolyalkylene glycols, polyethylene glycols (typically up to a molecular weight of about 600), glycolates, glycerol, sorbitan esters, esters of citric and tartaric acid, imidazoline derived amphoteric surfactants, lactams, amides, polyamides, quaternary ammonium compounds, esters such phthalates, adipates, stearates, palmitates, sebacates, or myristates and combinations thereof. Particularly preferred are polyhydric alcohols, polyethylene glycol (with a molecular weight up to about 600), glycerol, sorbitol, water and mixtures thereof.

Typically the adhesive comprises a ratio polymer to plasticiser by weight of from 1:100 to 100:1, more preferably from 50:1 to 1:50. However, the exact amounts and ratios of the polymer and plasticiser will depend to a large extent on the exact nature of polymer and plasticisers utilised and can be readily selected by the skilled person in the art. For example a high molecular weight polymer material will require a greater amount of plasticiser than a low molecular weight polymer.

In a preferred embodiment of the invention the plasticiser comprises any of the following either alone or in combination: at least one polymeric or non-polymeric polyhydric alcohol (such as glycerol), at least one ester derived therefrom and/or at least one polymeric alcohol (such as polyethylene oxide). Glycerol is the preferred plasticiser. An alternative preferred plasticiser is the ester derived from boric acid and glycerol. The plasticiser is generally used to plasticise the hydrogel compositions in accordance with the invention and control adhesive and electrical properties, for electrically conducting hydrogels. When water is lost from the hydrogel both the adhesive and electrical properties may change deleteriously. The reaction mixture preferably comprises from about 10% to about 50% and preferably from about 15% to about 45%, by weight of the reaction mixture, of plasticiser (other than water).

Water

The reaction mixture preferably comprises up to about 40% (e.g. from about 3% to about 40%), by weight of the reaction mixture, of water. The water acts both as a solvent and as a further plasticiser. The activity of the water may be varied by changing its concentration and/or the presence of the other components for example monomer, plasticiser and electrolyte, if present. Control of the activity of the water will allow variation in adhesion, the extent of water uptake with increasing residence time on the skin and the electrical properties of the gel.

One preferred feature of the process used in carrying out the invention is that to achieve the desired adhesive and electrical properties the final amount of water required in the hydrogel is present in the formulation prior to gellation, i.e. less than about 5% water is removed from the hydrogel after manufacture and less than about 10% during manufacture.

The water activity of the hydrogel can be measured using impedance methods with devices such as the Rotronic AWVC (manufactured by Rotronic). The activity of water may also be determined by placing the hydrogel in environments of controlled humidity and temperature and measuring the changes in weight. The relative humidity (RH) at which the hydrogel does not change weight corresponds to the activity of water in the gel (%RH/100). The use of saturated salt solutions to provide the appropriate environmental conditions is well known. All hydrogels directly exposed to relative humidities less than corresponding to the activity of water will be thermodynamically allowed to lose water. Exposure to greater relative humidities and the gel will gain weight. Water activity in the hydrogel is primarily dependent on the water content and the nature of the polymeric components and the way in which they are processed.

It has also been found that water activity influences the electrical properties. The higher the activity of water the lower the impedance (e.g. as measured at 10 Hz).

Cross-Linkers

The cross-lining agent(s), if present, will provide the necessary mechanical stability and will assist in controlling the adhesive properties of the hydrogel. Any di- or multifunctional free radical cross-linking agent may be used. Typical crosslinkers include tripropylene glycerol diacrylate, ethylene glycol dimethacrylate, triacrylate, polyethylene glycol diacrylate (PEG400 or PEG600), methylene bis acrylamide.

Surfactants

Any compatible surfactant may be used. Nonionic, anionic and cationic surfactants are preferred. The surfactant ideally comprises any of the surfactants listed below either alone or in combination with other surfactants.

1. Nonionic Surfactants

Suitable nonionic surfactants include, but are not limited to, those selected from the group consisting of the condensation products of a higher aliphatic alcohol, such as a fatty alcohol, containing about 8 to about 20 carbon atoms, in a straight or branched chain configuration, condensed with about 3 to about 100 moles, preferably about 5 to about 40 moles and most preferably about 5 to about 20 moles in ethylene oxide. Examples of such nonionic ethoxylated fatty alcohol surfactants are the Tergitol™ 15-S series from Union. Carbide and Brij™ surfactants from ICI. 15-S surfactants include $C_{11}$–$C_{15}$ secondary alcohol polyethyleneglycol ethers. Brij™ 58 surfactant is polyoxyethylene (20) cetyl ether, and Brij™ 76 surfactant is polyoxyethylene (10) stearyl ether.

Other suitable nonionic surfactants include, but are not limited to, those selected from the group consisting of the polyethylene oxide condensates of one mole of alkyl phenol containing from about 6 to 12 carbon atoms in a straight or branched chain configuration, with about 3 to about 100 moles of ethylene oxide. Examples of nonionic surfactants are the Igepal™ CO and CA series from Rhone-Poulenc. Igepal™ CO surfactants include nonylphenoxy poly (ethyleneoxy) ethanols. Igepal™ CA surfactants include octylphenoxy poly(ethyloneoxy) ethanols.

Another group of usable nonionic surfactants include, but are not limited to, those selected from the group consisting of block copolymers of ethylene oxide and propylene oxide or butylene oxide.

Examples of such nonionic block copolymer surfactants are the Pluronic™ and Tetronic™ series of surfactants from BASF. Pluronic™ surfactants include ethylene oxide-propylene oxide block copolymers. Tetronic™ surfactants include ethylene oxide-propylene oxide block copolymers. The balance of hydrophobic and hydrophilic components within the surfactant together with the molecular weight are found to be important. Suitable examples are Pluronic L68 and Tetronic 1907. Particularly suitable examples are Pluronic L64 and Tetronic 1107.

Still other satisfactory nonionic surfactants include, but are not limited to, those selected from the group consisting of sorbitan fatty acid esters, polyoxyethylene sorbitan fatty acid esters and polyoxyethylene stearates. Examples of such fatty acid ester nonionic surfactants are the Span™, Tween™, and Myrj™ surfactants from ICI. Span™ surfactants include $C_{12}$–$C_{18}$ sorbitan monoesters. Tween™ surfactants include poly(ethylene oxide) $C_{12}$-$C_{18}$ sorbitan monoesters. Myrj™ surfactants include poly(ethylene oxide) stearates.

2. Anionic Surfactants

Anionic surfactants normally include a hydrophobic moiety selected from the group consisting of(about $C_6$ to about $C_{20}$) alkyl, alkylaryl, and alkenyl groups and an anionic group selected from the group consisting of sulfate, sulfonate, phosphate, polyoxyethylene sulfate, polyoxyethylene sulfonate, polyoxyethylenephosphate and the alkali metal salts, ammonium salts, and tertiary amino salts of such anionic groups.

Anionic surfactants which can be used in the present invention include, but are not limited to, those selected from the group consisting of (about $C_6$ to about $C_{20}$) alkyl or alkylaryl sulfates or sulfonates such as sodium lauryl sulfate (commercially available as Polystep™ B-3 from Srepan Co.) and sodium dodecyl bezene sulfonate (commercially available as Siponate™ DS-10 from Rhone-Poulene); polyoxyethylene (about $C_6$ to about $C_{20}$) alkyl or alkylphenol ether sulfates with the ethylene oxide repeating unit in the surfactant below about 30 units, preferably below about 20 units, most preferably below about 15 units, such as Polystep™ B-1 commercially available from Stepan Co., and Alipal™ EP110 and 115 from Rhone-Poulenc (about $C_6$ to about $C_{20}$) alkyl or alkylphenoxy poly(ethyleneoxy)ethyl mono-esters and di-esters of phosphoric acid and its salts, with the ethylene oxide repeating unit in the surfactant below about 30 units, preferably below about 20 units, most preferably below about 15 units, such as Gafac™ RE-510 and Gafac™ RE-610 from GAF.

3. Cationic Surfactants

Cationic surfactants useful in the present invention include, but are not limited to, those selected from the group consisting of quaternary ammonium salts in which at least one higher molecular weight group and two or three lower molecular weight groups are linked to a common nitrogen atom to produce a cation, and wherein the electrically-balancing anion is selected from the group consisting of a halide (bromide, chloride, etc), acetate, nitrite, and lower (e.g. $C_1$ to $C_4$) alkosulfate (methosulfate etc). The higher molecular weight substituent(s) on the nitrogen is/are often (a) higher alkyl group(s), containing about 10 to about 20 carbon atoms, and the lower molecular weight substituents may be lower alkyl of about 1 to about 4 carbon atoms, such as methyl or ethyl, which may be substituted, as with hydroxy, in some instances. One or more of the substituents may include an aryl moiety or may be replaced by an aryl, such as benzyl or phenyl.

In a particular preferred embodiment of the invention the surfactant comprises at least one propylene oxide/ethylene oxide block copolymer, for example such as that supplied by BASF Plc under the trade name Pluronic L64. The reaction mixture preferably comprises from about 0.05% to about 10% and ideally from about 0.1% to about 5%, by weight of the reaction mixture, of surfactant.

The surfactant is believed to act to remove grease from the skin and to form the removed grease into isolated pockets within the hydrogel without reducing the work of adhesion of the coating.

Lipid-Micellising Polymers

In a further form of the invention the reaction mixture may further comprises from about 0.1% to about 5% by weight of the reaction mixture of a lipid-micellising polymer, i.e. a so-called hypercoiling polymer. This polymer functions to micellise and remove the rolled up pockets of grease from the gel-skin interface.

This hypercoiling polymer has the capability of more effectively solvating the primary surfactant micelles that contact hydrophobic skin contamination such as skin lipid or skin creme. The consequence of this functional role is that the work of adhesion between adhesive and skin is progressively less affected by the presence of either or both surfactant or hydrophobic skin contamination.

The hypercoiling polymer preferably comprises any of the following either alone or in combination: poly (maleic acid-styrene), poly (maleic acid-butyl vinyl ether), poly (maleic acid-propyl vinyl ether), poly (maleic acid-ethyl vinyl ether) and poly (acrylic acid-ethyl acrylate).

A particularly preferred example is an alternating copolymer of styrene and maleic acid.

Interpenetrants

Hydrogels based on interpenetrating polymer networks (IPN) are well known. The present invention is applicable to such systems. An IPN has been defined as a combination of two polymers, each in network form, at least one of which has been synthesised and/or crosslinked in the presence of the other. As will be appreciated, this combination will generally be a physical combination rather than a chemical combination of the two polymers IPN systems may be described by way of example as follows:

Monomer 1 is polymerised and crosslinked to give a polymer which is then swollen with monomer 2 plus its own crosslinker and initiator.

If only one polymer in the system is crosslinked the network formed is called a semi-IPN. Although they are also known as IPN's, it is only if there is total mutual solubility that full interpenetration occurs. In most IPN's there is, therefore, some phase separation but this may be reduced by chain entanglement between the polymers. It has also been reported that semi IPN's can be made in the presence of carrier solvents (for example water in the case of hydrophilic components).

Polymerising and crosslinking water soluble monomers in the presence of water soluble polymers, water and polyhydric alcohols produces hydrogel materials with enhanced rheological and consequently adhesive properties.

Suitable water soluble polymers for the formation of semi IPN's include poly (2-acrylamido-2-methylpropane sulphonic acid) or one of its salts and its copolymers, poly (acrylic acid-(3-sulphopropyl) ester potassium salt), copolymers of NaAMPS and SPA, polyacrylic acid, polymethacrylic acid, polyethylene oxide, polyvinyl methyl ether, polyvinyl alcohol, polyvinylpyrrolidone, its copolymers with vinyl acetate, dimethylaminoethyl methacrylate, terpolymers with dimethylaminoethyl methacrylate and vinylcaprolactam, polysaccharides such as gum arabic, karaya gum, xanthan gum, guar gum, carboxymethyl cellulose (CMC), NaCMC, hydroxypropylmethyl cellulose (HPMC), hydroxyethyl cellulose (HEC) or combination thereof.

The amount of interpenetrant polymer used will be dependent on the mechanical and rheological properties required as well as on consideration of processing conditions. If the interpenetrant polymer used increases the viscosity of the pre-gel mix beyond 5000 centipoise, the monomers do not polymerise and crosslink on an acceptable time scale (should be less than 60 seconds, preferably less than 10 seconds). The viscosity depends on the nature of molecular weight of the interpenetrant and the nature of pre-gel processing.

Of the natural polysaccharides, gum arabic is usually preferred due to its cold water solubility and lesser effect on viscosity compared with, for example, karaya gum. A higher concentration of gum arabic than karaya may therefore be used if desired, enabling a wider control of hydrogel properties. The processing steps for assembling the pre-gel formulation can be critical with respect to the properties of the manufactured hydrogel. For a given formulation, if the components are assembled at 25° C. and cured different electrical and adhesive properties are obtained compared to those that have been heated to 70° C. Whilst adhesive properties may be enhanced, electrical properties e.g. low frequency impedance, can be downgraded. Solutions containing natural polysaccharides become less opaque indicative of improved solubility. The activity of water in hydrogels prepared from heat treated pre-gels generally is lower than in non heat treated pre-gels.

Electrolytes

Any suitable electrolyte may be included in the bioadhesive composition, in an amount sufficient to provide or enhance electrical conductivity. Suitable electrolytes include water-soluble salts, particularly alkali metal salts such as sodium and potassium halide salts, most particularly sodium chloride or potassium chloride.

Other Additives

Additional functional ingredients may also be incorporated in the hydrogels of this invention, including antimicrobial agents (e.g. citric acid, stannous chloride) and, for drug delivery applications, pharmaceutically active agents, the latter being designed to be delivered either passively (e.g. transdermally) or actively (e.g. iontophoretically) through the skin.

Polymerisation with Cross-linking and/or Entanglement

The method of manufacture of the compositions of the invention generally involves free radical polymerisation and ideally would involve the use of photoinitiation or a combination of photoinitiation and thermal initiation. However, any free radical induced process of initiation may be used, for example Redox, thermal, electron beam and gamma or UV radiation. Preferably the reaction mixture comprises from 0.02% to 2%, and ideally from 0.02% to 0.2%, by weight of the reaction mixture of a photoinitiator. Preferably the reaction mixture comprises from 0.02% to 2%, and ideally from 0.02% to 0.2%, by weight of a thermal initiator. Preferred photoinitiators include any of the following either alone or in combination:

Type I-α-hydroxy-ketones and benzilidimethyl-ketals e.g. Irgacure 651. These are believed on irradiation to form benzoyl radicals that initiate polymerisation. Photoinitiators of this type that are preferred are those that do not carry substituents in the para position of the aromatic ring. Examples include Irgacure 184 and Darocur 1173 as marketed by Ciba Chemicals, as well as combinations thereof.

Photoinitiators of the following general formula are preferred:

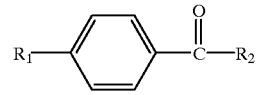

where $R_1$ can be any of the following: hydrogen, $H_3C-S-$,

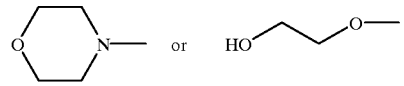

$R_1$ is most preferably hydrogen.
$R_2$ can suitably be any of the following:

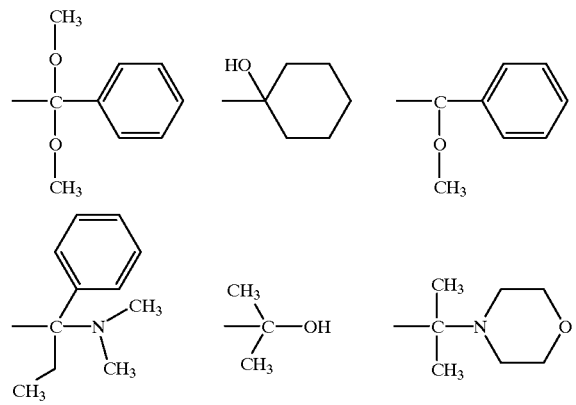

$R_2$ is most preferably as follows:-

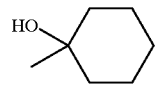

A particularly preferred photoinitiator is 1-hydroxycyclohexyl phenyl ketone; for example as marketed under the trade name Irgacure 184 by Ciba Speciality Chemicals. Also preferred are Darocur 1173 (2-hydroxy-2-propyl phenyl ketone) and mixtures of Irgacure 184 and Darocur 1173.

In preparing bioadhesive compositions in accordance with the invention, the ingredients will usually be mixed to provide a reaction mixture in the form of an initial pre-gel aqueous based liquid formulation, and this is then converted into a hydrogel by a free radical polymerisation reaction This may be achieved for example using conventional thermal initiators and/or photoinitiators or by ionizing radiation. Photoinitiation is a preferred method and will usually be applied by subjecting the pre-gel reaction mixture containing an appropriate photoinitiation agent to UV light after it has been spread or coated as a layer on siliconised release paper or other solid substrate. The incident UV intensity, at a wavelength in the range from 240 to 420 nm, is ideally substantially 40 mW/cm². The processing will generally be carried out in a controlled manner involving a precise predetermined sequence of mixing and thermal treatment or history.

The UV irradiation time scale should ideally be less than 60 seconds, and preferably less than 10 seconds to form a gel with better than 95% conversion of the monomers and for conversion better than 99.95% exposure to UV light less than 60 seconds and preferably less than 40 seconds is preferred. Those skilled in the art will appreciate that the extent of irradiation will be dependent on the thickness of the reaction mixture, concentration of photoinitiator and nature of substrate onto which the reaction mixture is coated and the source of UV.

These timings are for medium pressure mercury arc lamps as the source of UV operating at 100 W/cm. The intensity of UV between 240 nm and 420 nm reaching the surface of the substrate is at least 200 mW/cm$^2$ as measured on a Solascope from Solatell. For a given lamp, UV intensity is a function of the operating power and distance of the reaction mixture from the UV source.

As already described above, however, the polymerisation with cross-linking and/or entanglement conditions may be selected, having regard to the diagnostic tan delta gradient, to achieve the desired skin adhesion properties according to the present invention.

It is noted that although the adhesives of this invention are normally prepared as sheets, coatings or laminates, other and non-limiting forms of preparation include fibres, strands pellets or particles.

The coating may be on a wide variety of substrates for example siliconised paper, polyester, metal foil, non-woven fabric, foam or mesh. The coating may also be integrated into gel. The thickness of the coating is preferably in the range from 0.03 mm to 2.0 mm. The gel may be laid down onto a substrate web via a slot die.

Applications

The adhesives described herein may be used in a range of skin contact applications either unsupported, or in the form of supported layers, membranes, composites or laminates. Biomedical skin electrodes and medical skin coverings are mentioned in particular.

Such medical skin coverings include tapes, bandages and dressings of general utility, wound healing and wound management devices; skin contacting, ostomy and related incontinence devices and the like. Other fields of application include pharmaceutical delivery devices, for the delivery of pharmaceuticals or other active agents to or through mammalian skin, optionally containing topical, transdermal or iontophoretic agents and excipients. Particular bioadhesives may, for example, find application in buccal or gastrointestinal drug delivery systems. Non-limiting examples of penetration-enhancing agents include methyl oleic acid, isopropyl myristate, Azone® Transcutol® and N-methyl pyrrolidone.

It is preferred that the adhesives are supported as layers in use as biomedical skin electrodes or medical skin coverings.

Biomedical skin electrodes typically comprise a flexible planar conductive member rendered skin-adhesive by the presence of a layer of a conductive bioadhesive composition on the skin-directed face of the conductive member. The bioadhesive composition of the present invention may be used for this purpose, preferably with the inclusion of an electrolyte such as potassium chloride to enhance electrical conductivity. The conductive member may suitably include a synthetic material such as a polyester film or polyurethane foam and may include synthetic and/or natural fibres. The conductive member will typically include a finely divided conductivity enhancer such as a metal (e.g. as a finely divided powder or the like) or carbon powder. A metallised interface (e.g. silver/silver chloride) may suitably be provided between the conductive member and the adhesive layer, again to enhance conductivity.

Biomedical skin electrodes may be adapted to be electrically connected to an electrical diagnostic, therapeutic or electrosurgical apparatus, or to earth, via a connecting lead. The lead may be separably connectable to the electrode, or may be fixedly connected to the electrode.

An electrode adapted for separable connection to the connecting lead may, for example, include an electrically conductive tab which extends from the planar conductive member and which can be received in a suitably configured conductive clamp or clip connected to the connecting lead, e.g. a clip having sprung jaws which grip the tab and thereby establish the electrical connection between the electrode and the electrical apparatus or earth.

An alternative electrode adapted for separable connection to the connecting lead may, for example, include a metal or metal-plated stud or eyelet protruding through the flexible planar conductive member, the stud or eyelet being in electrical connection with the bioadhesive composition, suitably via a snap-fitted locking piece which locks the stud or eyelet to the conductive member by sandwiching at least a portion of the conductive member between the stud or eyelet and the snap-fitted locking piece. In this embodiment, the clip provided on the lead will be configured to engage with the stud or eyelet or alternatively a snap-fit device may be provided on the lead, which engages with the stud or eyelet.

An electrode having a fixed connecting lead may, for example, include a conductive lead having an insulating sheath which is configured to leave a bare end of a conductive lead core embedded in the planar conductive member. The end of the conductive lead may be electrically connected to a current distribution member embedded in the planar conductive member, e.g. as described in EP-A-0012402, the disclosure of which is incorporated herein by reference.

Any electrical lead connecting the biomedical skin electrode to an electrical diagnostic, therapeutic or electrosurgical apparatus, or to earth, may itself be arranged in two or more releasably connected portions if convenient.

The layer of bioadhesive composition on the biomedical skin electrode may suitably be protected before use by an protective release layer. For use, the release layer is removed and the bioadhesive composition of the invention-on the skin-directed face of the conductive member-is applied to the skin of the patient, whereby the electrode becomes attached to the skin.

The discussion above of various possible types of skin electrode is non-limiting. The bioadhesive composition of the present invention may be employed with all shapes and configurations of skin electrodes. In addition to the prior art references cited above, describing specific types of skin electrode, reference is also directed to WO-A-97/24149 (Minnesota Mining and Manufacturing Company), the disclosure of which is incorporated herein by reference, and particularly FIGS. 1 to 5 thereof and the associated description, which illustrate some of the conventional shapes and configurations of biomedical skin electrode in which the bioadhesive composition of the present invention may be used. These illustrated electrodes are separable from a connector lead which electrically connects the conductive medium to the electrical equipment or to earth.

When the hydrogels are intended for use in conjunction with Ag/AgCl medical electrodes, chloride ions are required to be present in order for the electrode to function. Potassium chloride and sodium chloride are commonly used. However any compound capable of donating chloride ions to the system may be used, for example, lithium chloride, calcium chloride, ammonium chloride. The amount that should be added is dependent on the electrical properties required and is typically 0.2% to 8% and preferably 1% to 7% by weight.

The main electrical property of interest is the impedance. Performance standards have been drawn up by the American Association of Medical Instruments (AAMI). In sensing electrode applications the electrodes, consisting of the adhesive and a suitable conductive support, are placed in pairs, adhesive to adhesive contact. The conductive support frequently has a Ag/AgCl coating in contact with the adhesive. The measured impedance is dependent on both the quality of the Ag/AgCl coating and the adhesive. In this configuration the adhesive must contain chloride ions. The concentration of chloride ions influences the impedance such that increasing the concentration can lower impedance. It would be anticipated that the activity of the ions (as opposed to the concentration) would be important in determining impedance, but in practice the determination of ion activity in these systems is not a trivial matter. In designing the hydrogel for lowest impedance as measured under the AAMI standard, allowance must be given for the amount and activity of water. These factors will control the effective ion activity and hence the amount of chloride available for participating in the electrochemistry of the system. Hydrogels with lower chloride concentration but higher water activity have lower impedances.

A further application is in the field of medical skin coverings.

Medical skin coverings are useful for treatment of mammalian skin or mammalian skin openings, particularly against the possibility of infection and also for the transmission of moisture vapour and exudates from the skin. The medical skin coverings generally comprise a backing material onto which a layer of the bioadhesive composition of the invention is coated, the bioadhesive composition being protected before use by a protective release layer. The bioadhesive composition may, for example, include antimicrobial agents. For use, the release layer is removed and the bioadhesive composition of the invention is applied to the skin of the patient as part of a medical tape, a wound dressing, a bandage of general medicinal utility, or other medical device having moisture absorbing properties.

The bioadhesive composition layer may be coated on a layer of backing material selected from a range of suitable backing materials for use as medical tapes, dressings, bandages and the like. Suitable backing materials include those disclosed in U.S. Pat. Nos. 3,645,835 and 4,595,001, the disclosures of which are incorporated herein by reference. In addition to these prior art references, reference is also directed to WO-A-97/24149, and particularly FIG. 6 thereof and the associated description, which illustrates a conventional configuration of a medical skin covering in which the bioadhesive composition of the present invention may be used.

EXAMPLES OF THE INVENTION

The invention will be further described without limitation, with reference to the following Experiments, Examples and Test Methods.

Experiment A—Identification of a Diagnostic Tan Delta Minimum

The formulation detailed below was coated onto polyurethane foam (EV1700X from Caligen) at a coat weight of 0.8 to 1.6 kg per square meter and cured by exposure to ultraviolet radiation emitted from a medium pressure mercury arc lamp operating at 100 W/cm power for 10 seconds.

Example 1

Mix 6.0 g of Irgacure 184 with 20 g IRR280(PEG400 diacrylate) from UCB (Solution A) To 0.07 g of Irgacure 184 add 23.5 g of NNDMA and stir for one hour (keep container covered from light). Add 30 g of glycerol to this and stir for 5 minutes, followed by 40 g of NaAMPS (58% solution). Stir for another 5 minutes. Add 0.13 g of Solution A and stir the whole formulation for 1 hour before use.

Table 1

Effect of water uptake on peel adhesion on dry skin for the formulation in Example 1.

| % Water uptake | Peel Adhesion (N/cm) |
|---|---|
| Subject 1 | |
| 0 | 1.8 |
| 9 | 2.2 |
| 10 | 2.3 |
| 24 | 1.6 |
| Subject 2 | |
| 0 | 1.6 |
| 9 | 2.9 |
| 11 | 2.5 |
| 12 | 2.6 |

Peel Adhesion Method

This is a method to determine the peel strength required of adhered hydrogel to the skin of two male subjects of different ethnic origin. The skin is tested "dry" (i.e. normal to the subject) as described next.

Equipment

| | |
|---|---|
| Scissors | Convenient source |
| Standard ruler | Convenient source |
| Compression weight | 5.0 kg, diameter 130 mm |
| Polyester Film | PET 23μ available from EFFEGIDI S.p.A. 43052 Colomo, Italy |
| Transfer Adhesive | 3M 1524 available from 3M Italia S.p.A. 20090 Segrate, Italy |
| Stop Watch | Convenient source |
| Tensile Tester | Instron mod: 6021 (or equivalent) |

Test Procedure

| A) Tensile Tester Peel Settings:- | |
|---|---|
| Load cell | 10 N |
| Test Speed | 1000 mm/min |
| Clamp to Clamp Distance | 25 mm |
| Pre Loading | 0.2 N |
| Test Path "LM" | 50 mm |
| Measure variable | F average (N) in "LM" |

B) Sample Preparation

1. Each test specimen should be prepared individually and tested immediately.
2. Prepare rectangular adhesive samples 100 mm±2 length and 25.4 mm width.
3. The specimen is placed into an oven at 37° C. and at 85% humidity. The time of exposure is dependant on the degree of water uptake required. The sample is then removed from the oven and the steps 4 to 6 are carried out.
4. Attach adhesive specimen to the forearm within marked area with light pressure.
5. Gently roll the compression weight down the forearm, on the adhesion sample.

6. Remove the weight and test after 1 and 10 minutes by attaching one end of the specimen into the upper jaws of an adhesion testing machine at an initial angle of 90°.

The rheology of the compositions of the invention will be further exemplified with reference to the accompanying drawings in which.

Comparison Example A

Mix 6.0 g of Irgacure 184 with 20 g IRR280 (PEG 400 diacrylate) from UCB (Solution A). To 23 g of glycerol, 10 g of an ethylene/vinyl acetate copolymer emulsion (50% solids) (product of Harco Chemicals marketed under the trade name DM 137) are added, followed by 40 g of NaAMPS (58% solution) and 20 g of the potassium salt of 3-sulpho-propyl acrylate (SPA) with stirring. To this solution there are added 0.15 g of Solution A. The final solution is stirred for one hour and coated and cured as for Example 1 above.

Figure 1:
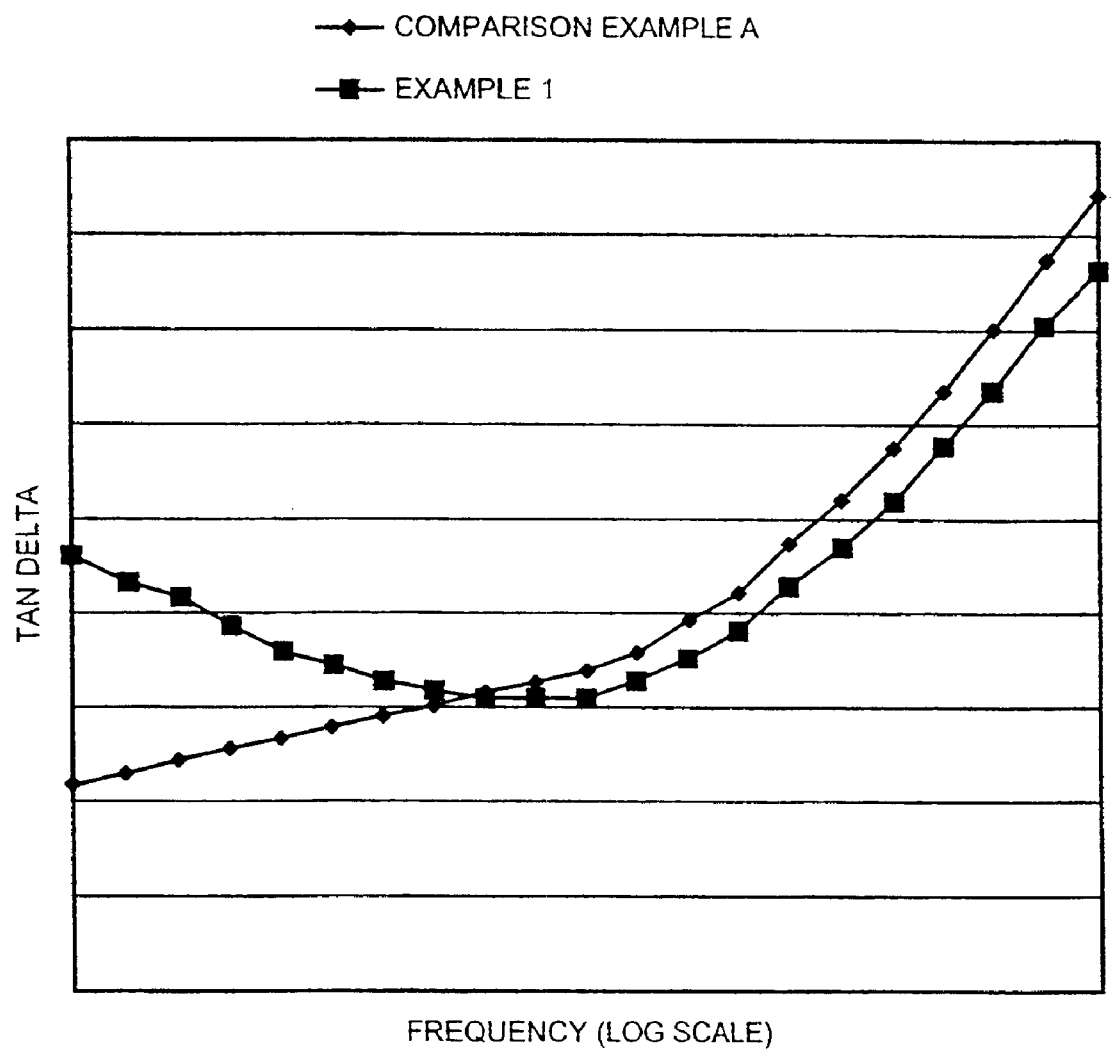
FIG. 1 shows schematic tan delta profiles for hydrogels exhibiting adhesion loss (comparison "Example A") and adhesion increase (Example 1) on water uptake.
Figure 2:
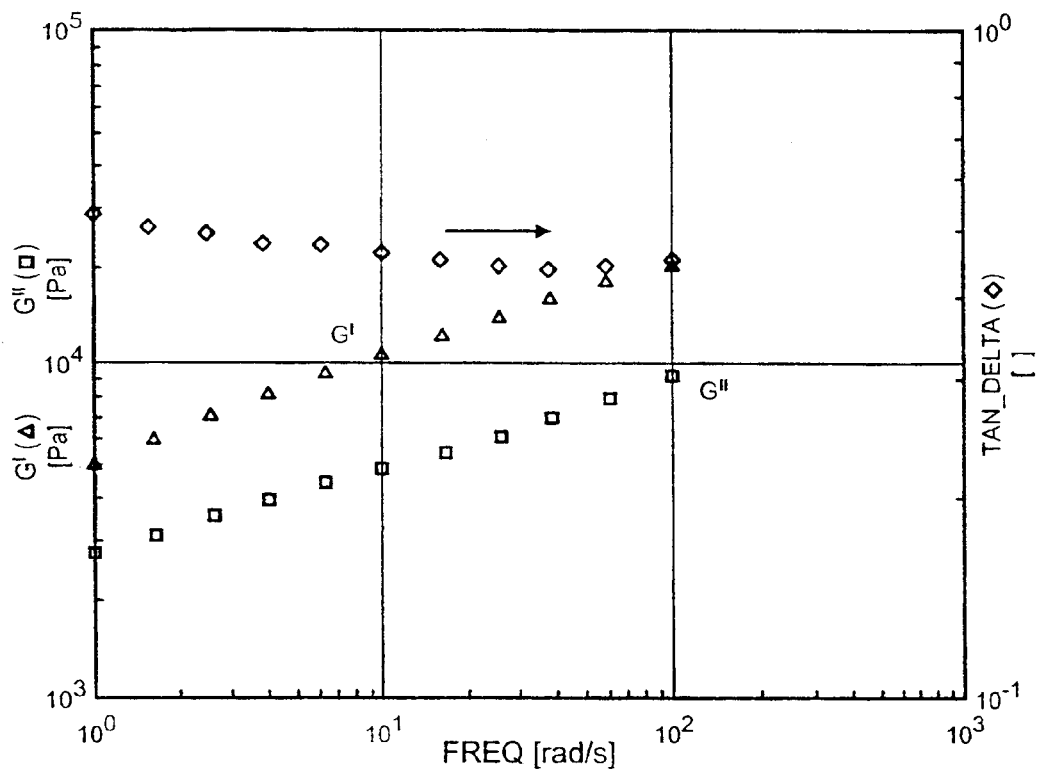
FIG. 2 shows plots of G', G" and tan delta against frequency for the freshly made hydrogel of above Example 1.
Figure 3:
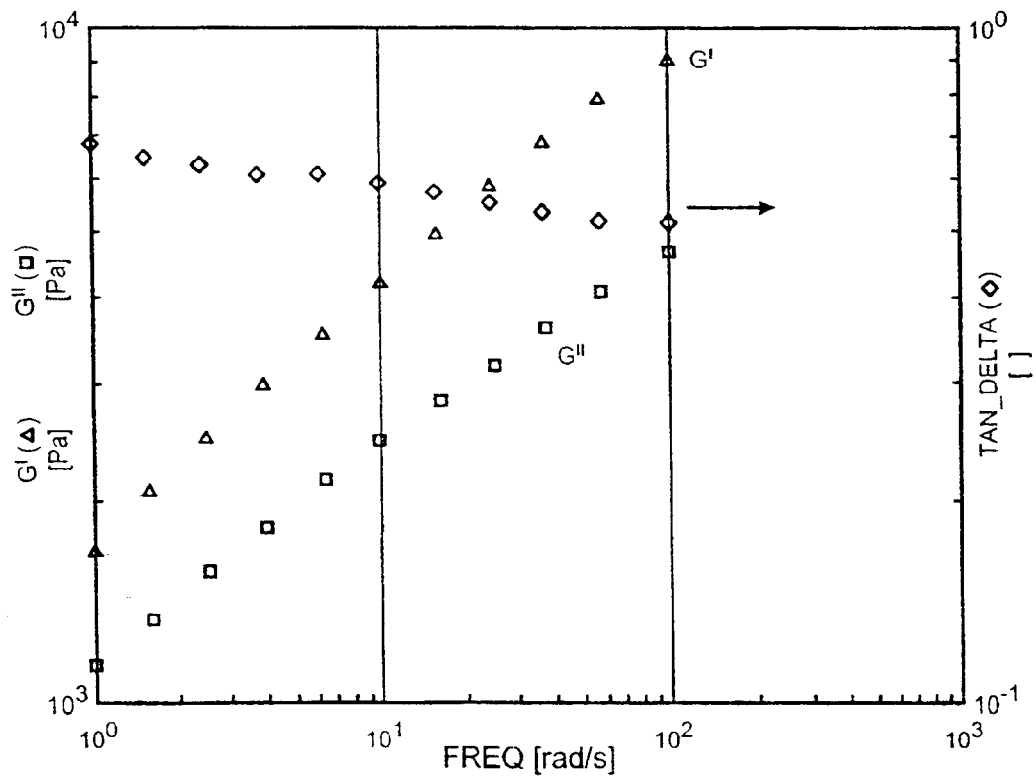
FIG. 3 shows plots of G', G", and tan delta against frequency for the freshly made hydrogel of above Example 1 after 7% water uptake.

As shown in FIG. 2, the tan delta curve exhibits a minimum at a frequency of about 50 rad/s, i.e. a single (zero gradient) minimum over the diagnostic range 0.01 to 100 rad/s. As shown in FIG. 3, this minimum is generally lost as water uptake proceeds.

Experiment B—Identification and Adjustment of a Diagnostic Tan Delta Gradient

Examples 2 and 3 Formulations (All Figures are Weights in Grams)

| Example | NaAMPS (58%) | SPA | Polyethylene Glycol (MWt 400) | KCl | IRR 280 | Irgacure 184 |
|---|---|---|---|---|---|---|
| 2A | 57 | 10 | 20 | 3 | 0.062 | 0.02 |
| 2B | 57 | 10 | 20 | 3 | 0.069 | 0.02 |
| 2C | 57 | 10 | 20 | 3 | 0.077 | 0.02 |
| 2D | 57 | 10 | 20 | 3 | 0.085 | 0.02 |
| 2E | 57 | 10 | 20 | 3 | 0.092 | 0.02 |
| 2F | 57 | 10 | 20 | 3 | 0.1 | 0.02 |
| 2G | 57 | 10 | 20 | 3 | 0.138 | 0.02 |

| Example | NaAMPS (50%) | | Glycerol | | IRR 210 | Irgacure 184 |
|---|---|---|---|---|---|---|
| 3A | 68.5 | 0 | 31.5 | 0 | 0.062 | 0.02 |
| 3B | 68.5 | 0 | 31.5 | 0 | 0.077 | 0.02 |
| 3C | 68.5 | 0 | 31.5 | 0 | 0.092 | 0.02 |
| 3D | 68.5 | 0 | 31.5 | 0 | 0.108 | 0.02 |
| 3E | 68.5 | 0 | 31.5 | 0 | 0.115 | 0.02 |

Method of Preparation, Example 2
1. 0.02 g of Irgacure 184 is dissolved in relevant weight of a PEG400 diacrylate crosslinker (IRR 280, from UCB) and is designated Solution A.
2. NaAPS (58% solution) is mixed with SPA, KCl and polyethyleneglycol (PEG400) using a mechanical stirrer for at least half an hour and then the appropriate amount of Solution A is added The solution is stirred for a further minimum of one hour before it is extruded from a slot die(coat weight approximately 1 kg per square meter) onto release paper and cured by passing under 3 100 W/cm medium pressure mercury arc lamps at a speed of 7 m/minute.

Method of Preparation, Example 3
1. 0.02 g of Irgacure 184 is dissolved in relevant weight of a triacrylate crosslinker (IRR 210) and is designated Solution A.
2. NaAMPS (50% solution) is mixed with glycerol using a mechanical stirrer for at least half an hour and then the appropriate amount of Solution A is added. The solution is stirred for a further minimum of one hour before it is extruded from a slot die (coat weight approximately 1 kg per square meter) onto release paper and cured by passing under 3 100 W/cm medium pressure mercury arc lamps at a speed of 7 m/minute.

Circular samples of each composition (25 mm diameter) are then cut and placed between parallel plates of a Rheometrics SR5 Rheometer (controlled stress parallel plate rheometer).

The results of the tan delta measurements are shown as follows.

FIGS. 4A to 4G show plots of G', G" and tan delta against frequency for the freshly made hydrogels of Examples 2A to 2G respectively.

FIGS. 5A to 5E show plots of G', G" and tan delta against frequency for the freshly made hydrogels of Examples 3A to 3E respectively.

Figure 4A:
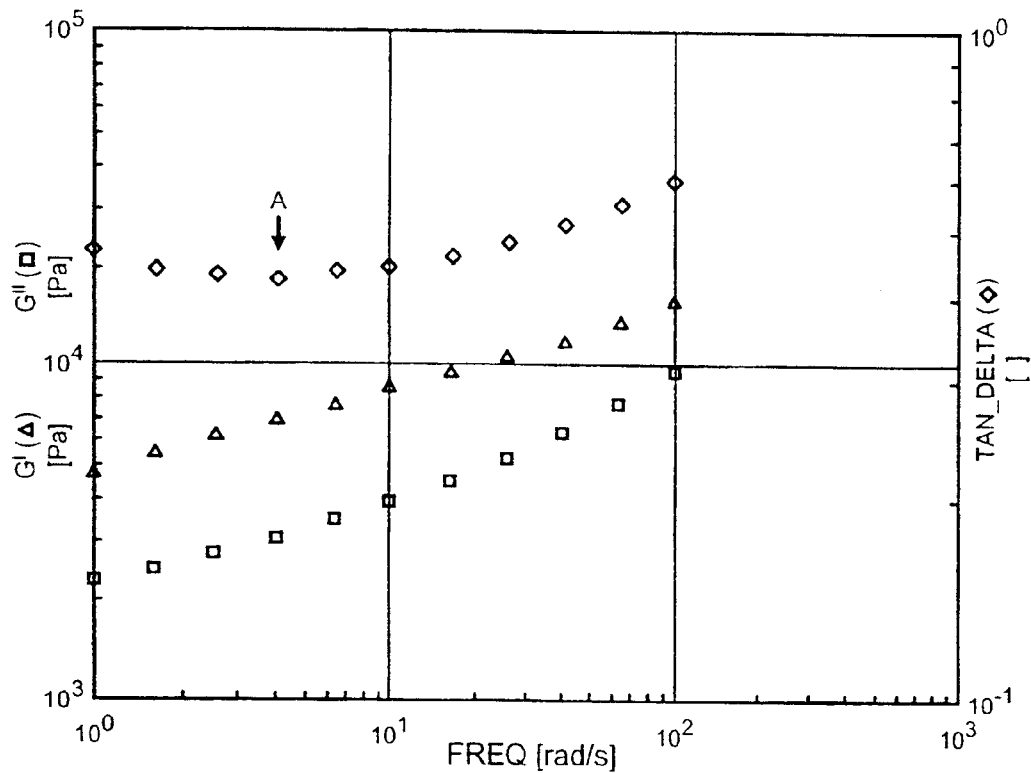
Figure 4B:
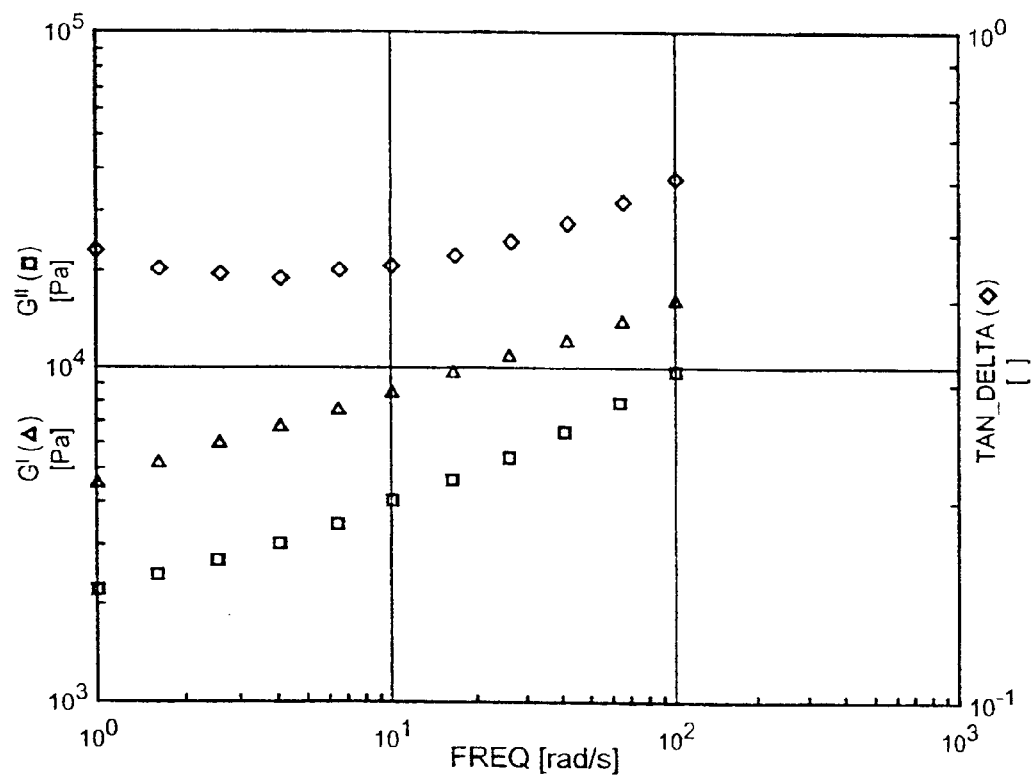
Figure 4C:
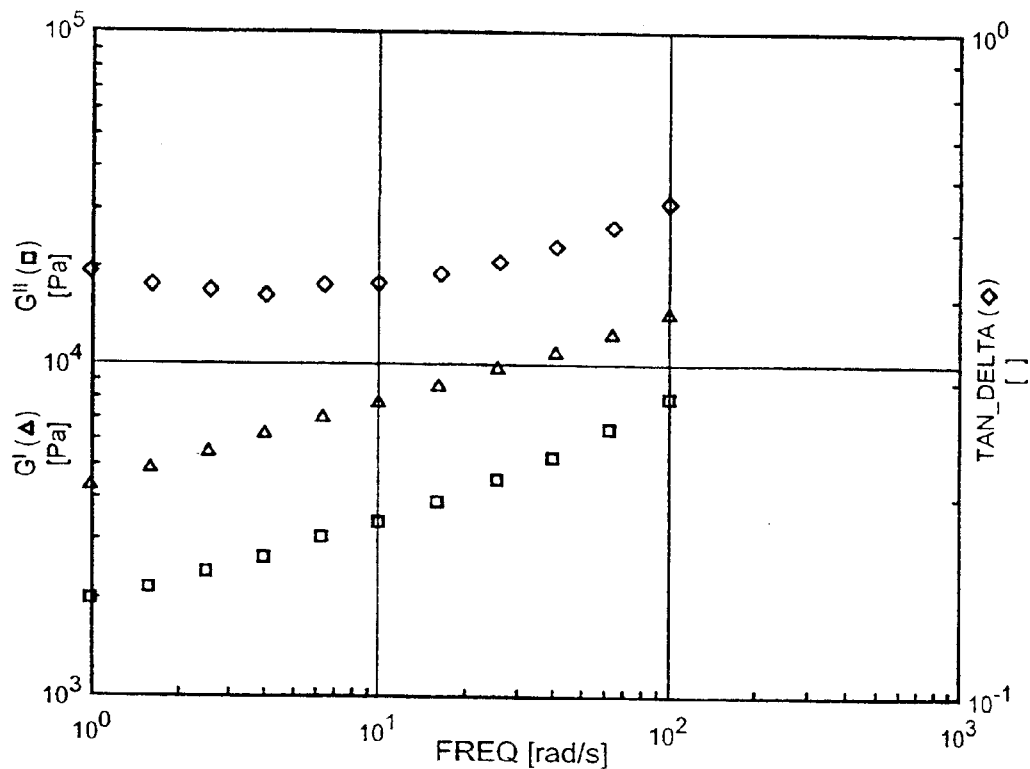
Figure 4D:
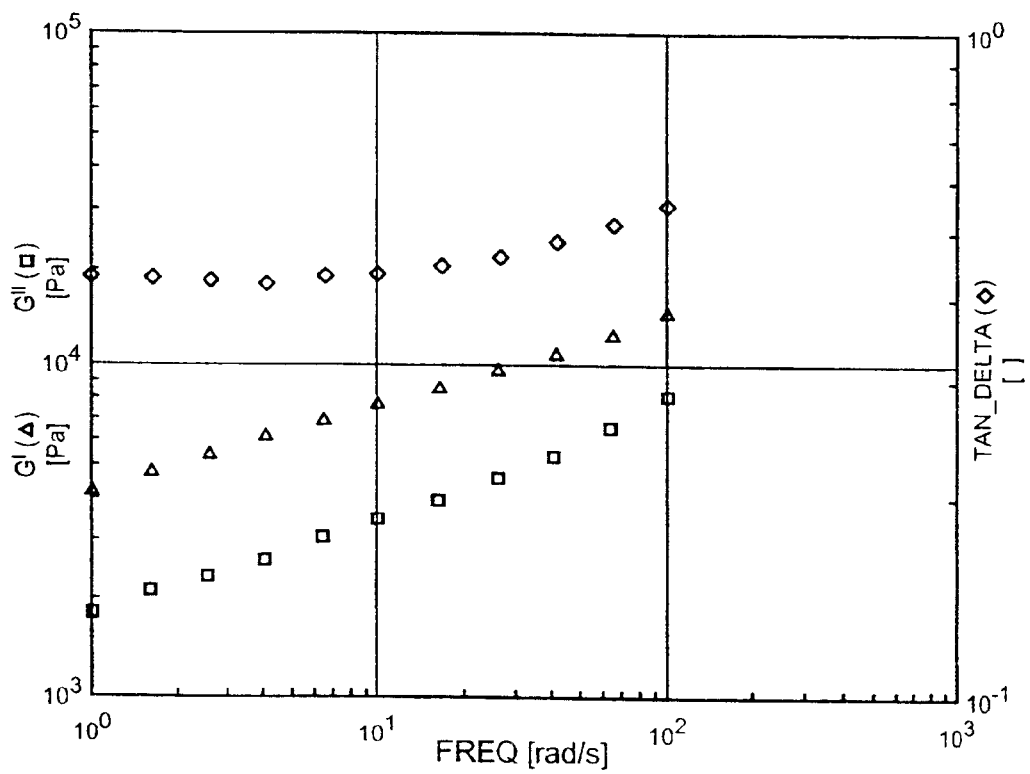
Figure 4E:
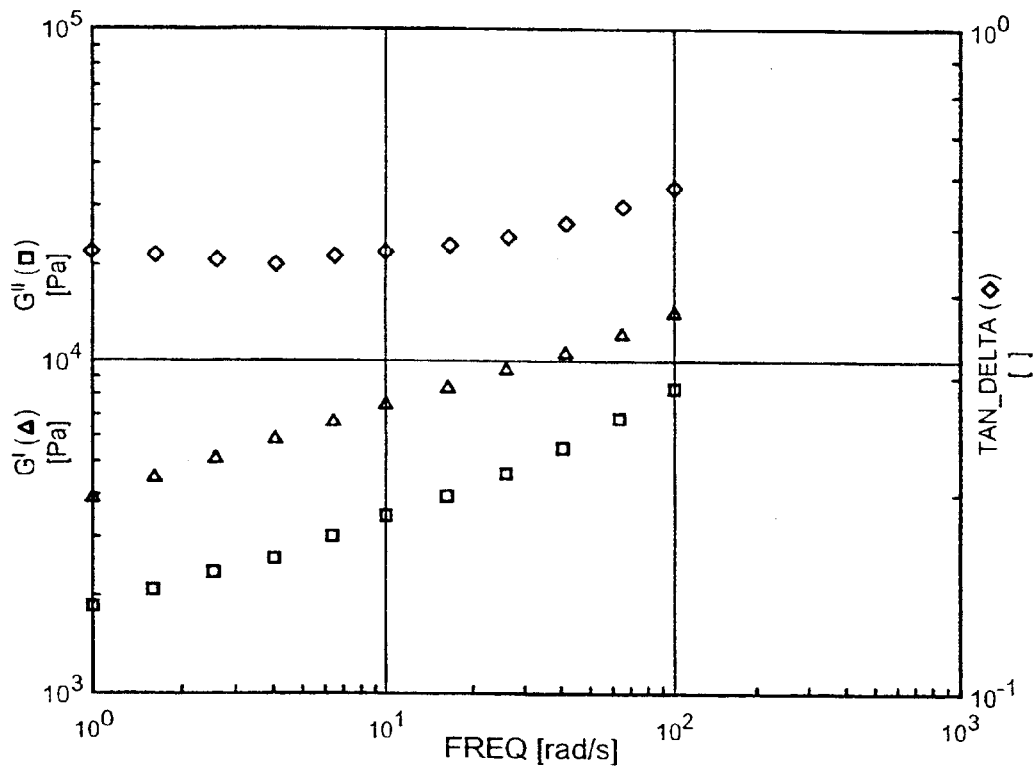
Figure 4F:
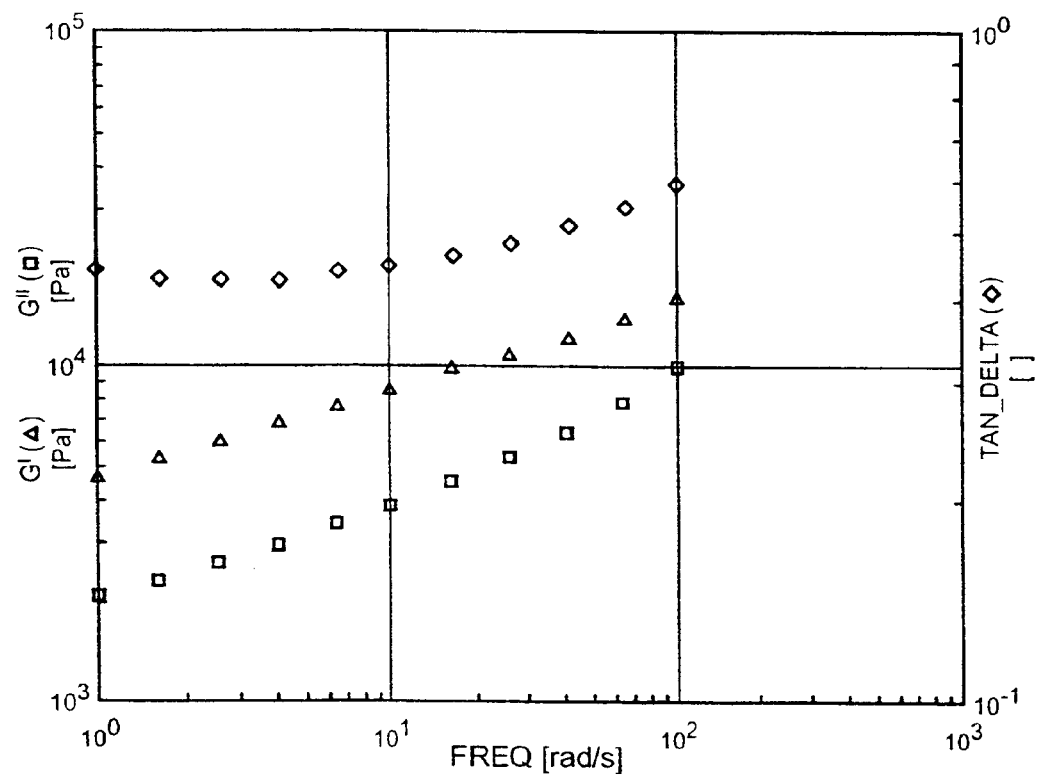
Figure 4G:
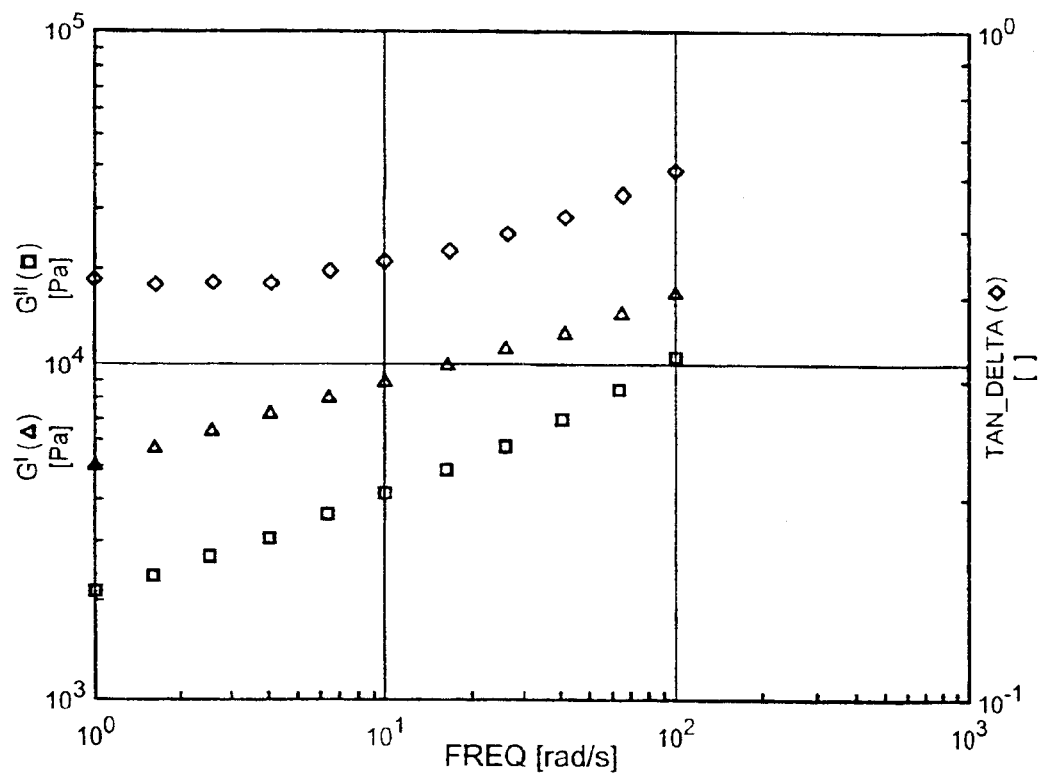
Figure 5A:
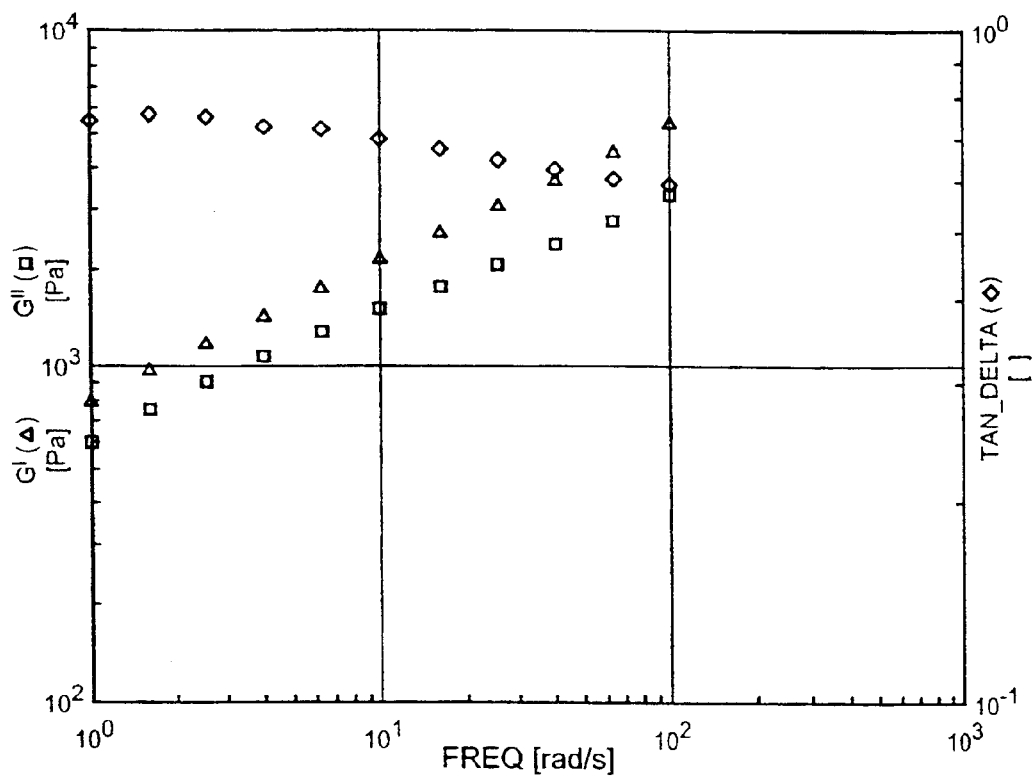
Figure 5B:
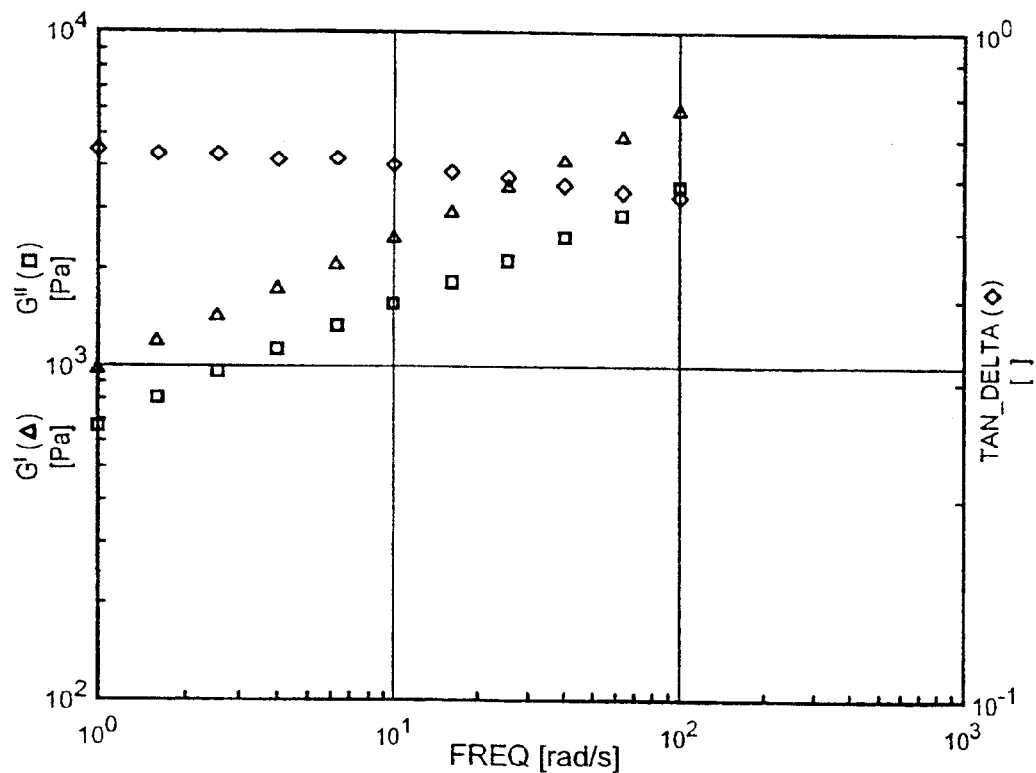
Figure 5C:
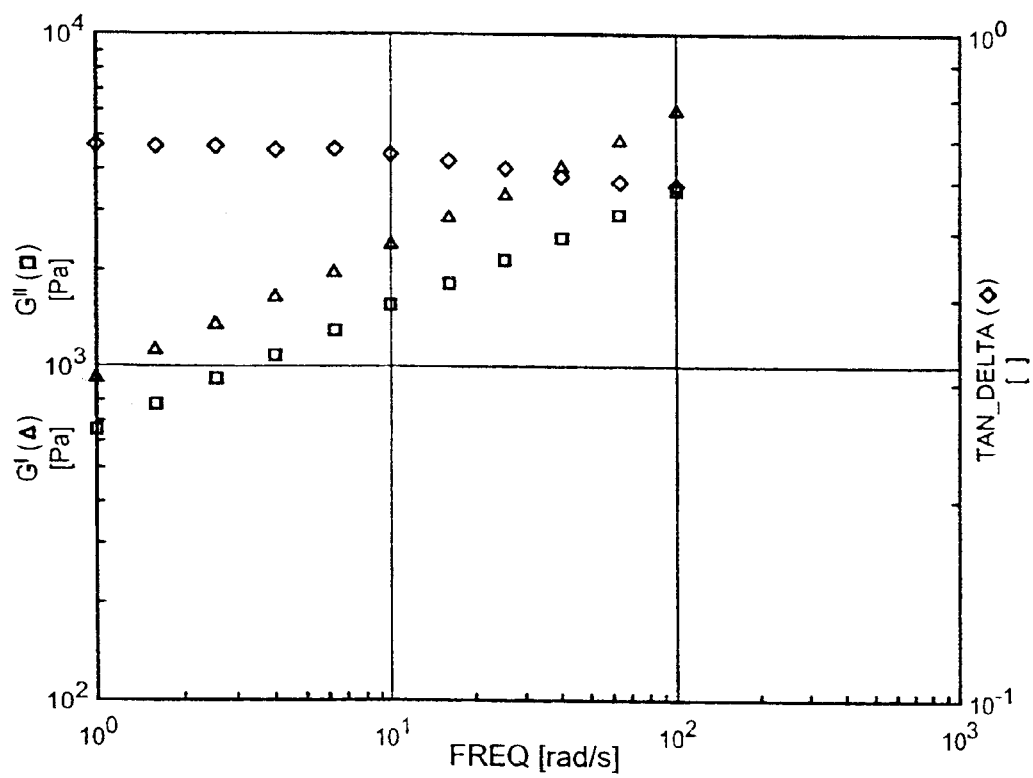
Figure 5D:
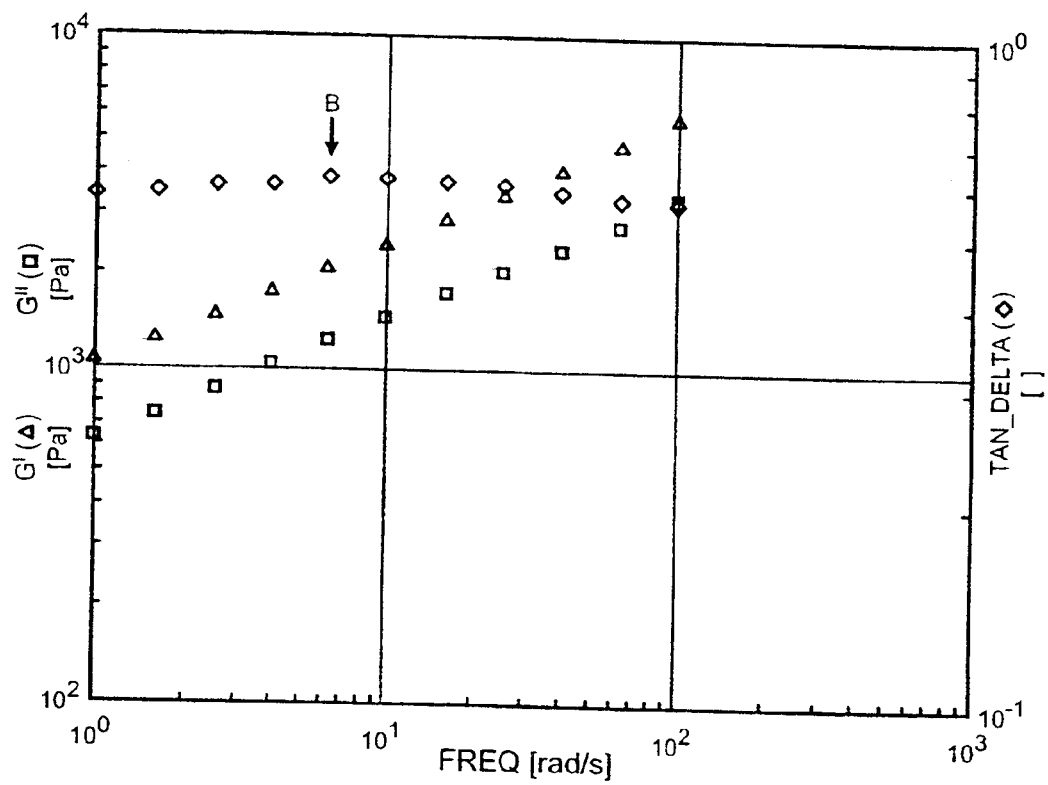
Figure 5E:
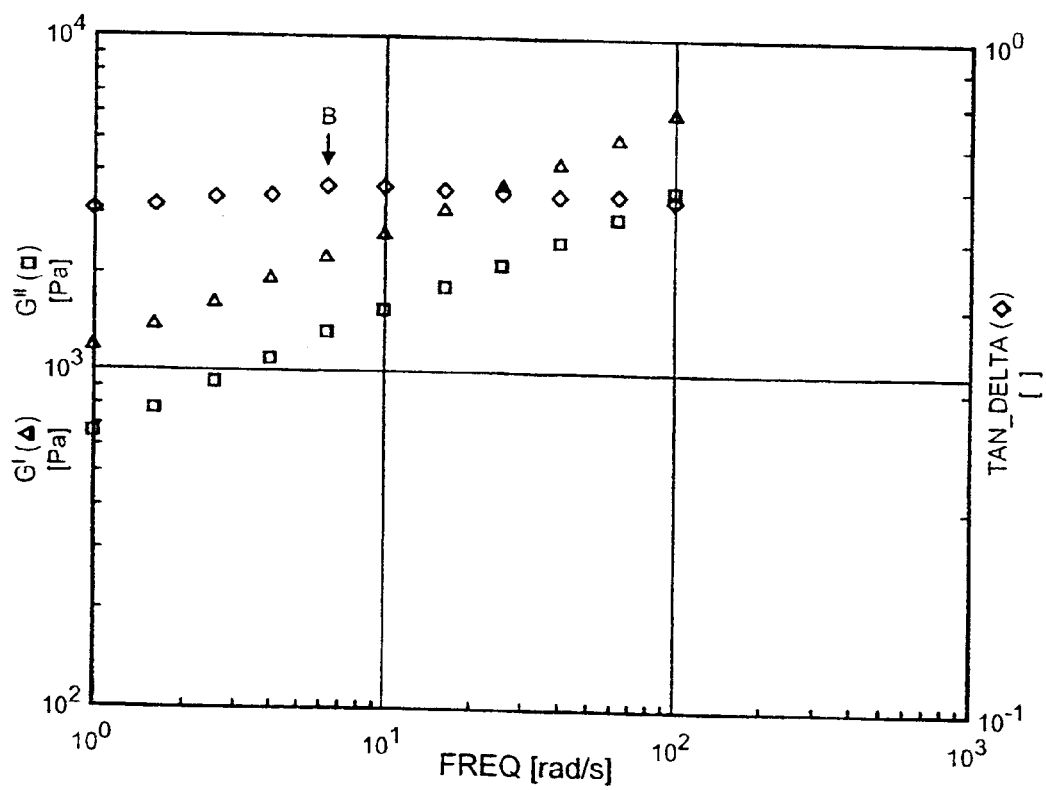
Figure 6:
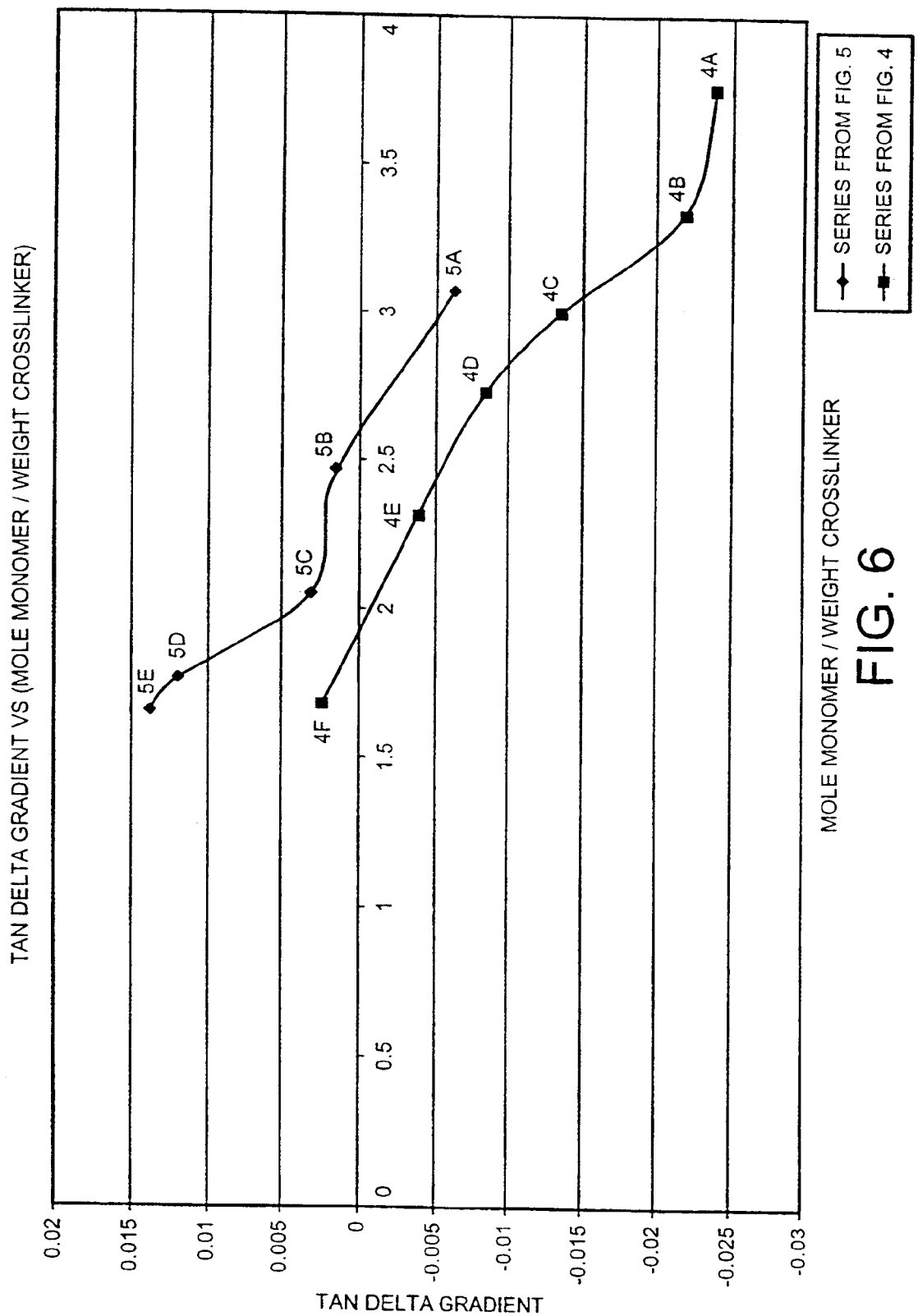

FIG. 6 shows plots of tan delta gradient v. ratio M:XL (mole M:weight XL), using data from FIGS. 4 and 5, the respective FIGS. 4A to 4F and 5A to 5E being noted at the points plotted.

In FIGS. 4A through to 4G, the variation in tan delta (top curve, marked by diamond shapes) can be clearly seen as the amount of cross-linking agent (and thereby the extent of cross-linking in the polymer) increases. The diagnostic portion of the frequency range 0.01 to 300 rad/s is here the sub-range 1 to about 4 rad/s. (Note that each axis follows a logarithmic scale). Within the range 0.01 to 300 rad/s a single minimum (A) can be seen in FIG. 4A, which disappears gradually and is lost by FIG. 4G. Moreover, the negative slope of the tan delta gradient of FIG. 4A in the diagnostic frequency range 1 to about 4 rad/s (i.e. frequencies below the frequency of the minimum A) is also gradually lost as the amount of cross-linking agent (and thereby the extent of cross-linking in the polymer) increases. By FIG. 4G there is no discernable slope to the tan delta gradient in the diagnostic range 1 to about 4 rad/s, i.e. the gradient has reduced to zero.

In FIGS. 5A through to 5E, the variation in tan delta (top curve, marked by diamond shapes) can be clearly seen as the amount of cross-linking agent (and thereby the extent of cross-linking in the polymer) increases. The diagnostic portion of the frequency range 0.01 to 300 rad/s is here the sub-range 1 to about 5 rad/s (note again that each axis follows a logarithmic scale). Within this diagnostic portion, an increase in the extent of cross-linking (FIGS. 5D and 5E) results in the appearance of a positive slope of tan delta against frequency. Thus, within the range 0.01 to 300 rad/s the more cross-linked compositions exhibit a single maximum (B) at a frequency of about 5 rad/s, a feature characteristic of water-unstable compositions which will lose adhesion to a substantial degree on uptake of water from the surrounding environment.

A comparison of the individual plots of G' and G" in FIGS. 5A through to 5E shows that there is a substantial change in the gradient of the G' plot against frequency, the low frequency values of G' being markedly reduced in the polymers having lower degree of cross-linking. This effect is observed to a lesser extent in the example shown in FIGS. 4A through to 4G.

FIG. 6 shows a plot of tan delta v. ratio M:XL (ratio expressed as moles of monomer M to weight of cross-linking agent XL) within the range 1 to 4. Data from FIGS. 4A to 4G and 5A to 5E were used to construct FIG. 6. The upper curve relates to FIGS. 5A to 5E and the lower curve relates to FIGS. 4A to 4G.

It can be clearly seen that the tan delta gradient in the respective diagnostic portion of the frequency range (1 to 4 rad/s for FIGS. 4A to 4G and 1 to 5 rad/s for FIGS. 5A to 5E) crosses the zero gradient from a negative gradient to a positive gradient as the amount of cross-linking agent is increased (i.e. the ratio M:XL is reduced).

Experiment C—Characterisation of Tan Delta Curves for Selected Hydrogels

A range of hydrogel compositions is prepared and the tan delta gradient in the diagnostic frequency region determined. From this, each hydrogel is characterised by whether or not it exhibits a tan delta minimum or negative slope in the diagnostic portion of the frequency range 0.01 to 300 rad/s. By selecting appropriate levels of cross-linking agent and photoinitiator, the tan delta minimum or negative slope can be arranged to be present or absent, as desired.

Examples 4 to 13 Formulations (All Figures are Parts by Weight)

| Example No. | 4 | 5 | 6 | 7 | 8 | 9 | 10 | 11 | 12 | 13 |
|---|---|---|---|---|---|---|---|---|---|---|
| Glycerol | 33 | 33 | 33 | 33 | 33 | 33 | 33 | 33 | 33 | 33 |
| Sodium AMPS | 39 | 39 | 19.3 | 19.3 | 19.3 | 19.3 | | | | |
| N,N-Dimethyl acrylamide | | | 19.3 | 19.3 | | | | | 33.5 | 33.5 |
| 3-sulphopropyl acrylate, potassium salt | | | | | | | 39 | 39 | | |
| Diacetone acrylamide | | | | | 19.3 | 19.3 | | | | |
| Sodium vinyl sulphonate | | | | | | | | | 8 | 8 |
| Water | 28 | 28 | 28 | 28 | 28 | 28 | 28 | 28 | 25.5 | 25.5 |
| Irgacure 184/IRR280 | 0.06 | 0.25 | 0.06 | 0.18 | 0.06 | 0.18 | 0.06 | 0.18 | 0.06 | 0.18 |

Method of Preparation Examples 4 to 13

1. 6 parts of Irgacure 184 are dissolved in 20 parts of a PEG 400 diacrylate crosslinker (IRR280 from UCB) and the resulting solution is designated Solution A.

2. Monomers, water and glycerol are mixed in the proportions indicated in the table above using a mechanical stirrer for at least half an hour and then the appropriate amount of Solution A is added. The solution is stirred for a further minimum of one hour before being extruded from a slot die (coat weight approximately 1 kg per square meter) onto release paper and cured by passing under 3 100 W/cm medium pressure mercury arc lamps at a speed of 7 m/minute.

Results

As a result of tan delta measurements analogously to those described in connection with Experiment B above, the formulations are characterised as follows.

| Example No. | 4 | 5 | 6 | 7 | 8 | 9 | 10 | 11 | 12 | 13 |
|---|---|---|---|---|---|---|---|---|---|---|
| Tan Delta Minimum or negative slope | Yes | No | Yes | No | Yes | No | Yes | No | Yes | No |

As will be seen, the invention presents a number of different aspects and it should be understood that it embraces within its scope all novel and inventive features and aspects herein disclosed, either explicitly or implicitly and either singly or in combination with one another. Also, many detailed modifications are possible and, in particular, the scope of the invention is not to be construed as being limited by the illustrative example(s) or by the terms and expressions used herein merely in a descriptive or explanatory sense.

What is claimed is:

1. A method for preparing a bioadhesive composition for use as a skin adhesive, the method comprising:

forming an aqueous reaction mixture comprising at least one monomer dissolved or suspended therein and capable of forming a hydrogel on polymerization, optionally at least one cross-linking agent for the monomer, and water; and polymerizing with cross-linking and/or entanglement the aqueous reaction mixture, wherein the degree of polymerization and/or the degree of cross-linking and/or entanglement are selected to control the skin adhesion properties of the bioadhesive composition by comparing the rate of change of tan delta ($G''/G'$) against frequency with the frequency range 0.01 to 300 rad/s to determine the diagnostic portion fo the frequency range, where $G''$ is the viscous modulus of the bioadhesive composition and $G'$ is the elastic modulus of the bioadhesive composition.

2. A method for controlling the skin adhesion properties of a bioadhesive composition for use as a skin adhesive, the method comprising polymerizing with cross-linking and/or entanglement an aqueous reaction mixture comprising at least one monomer dissolved or suspended therein and capable of forming a hydrogel on polymerization, optionally at least one cross-linking agent for the monomer, and water; wherein the reaction is conducted so that the degree of polymerization and/or the degree of cross-linking and/or entanglement are selected to control the skin adhesion properties of the bioadhesive composition by comparing the rate of change of tan delta (G"G') against frequency with the frequency range 0.01 to 300 rad/s to determine the diagnostic portion of the frequency range, where G" is the viscous modulus of the bioadhesive composition and G' is the elastic modulus of the bioadhesive composition.

3. The method of claim 1, wherein the desired degree of polymerization and/or the degree of cross-linking and/or entanglement in the polymerized composition is achieved by selection of the amount of monomer in the aqueous reaction mixture, the amount of any cross-linking agent present in the aqueous reaction mixture, anchor the reaction conditions for the polymerization with cross-linking and/or entanglement.

4. The method of claim 1, wherein the diagnostic portion of the frequency range is less than about 100 rad/s.

5. The method of claim 4, wherein the diagnostic portion of the frequency range is less than about 30 rad/s.

6. The method of claim 4, wherein the diagnostic portion of the frequency range is less than about 10 rad/s.

7. The method of claim 1, wherein the measurement of elastic modulus and viscous modulus is carried out at a temperature of about 37C.

8. The method of claim 3, wherein a cross-linking agent is present in (he aqueous reaction mixture and the relative amount of monomer and cross-linking agent is selected to achieve the desired degree of cross-linking.

9. The method of claim 8, wherein a cross-linking agent is present in the aqueous reaction mixture and the molar ratio of monomer(s) to cross-linking agent(s) is selected within the range of about 10,000:1 to about 200:1.

10. The method of claim 3, wherein the reaction conditions for the polymerization with cross-linking and/or entanglement are selected by controlling one or more of the following aspects of the polymerization reaction:
the reactivity of the monomer(s) and the number of polymerizable functions per molecule;
the reactivity of the cross-linking agent(s) and the number of reactive functions per molecule;
the presence of any polymerization inhibitor(s);
the presence of any chain-transfer agent(s);
the weight fraction of monomer(s) and cross-linking agent(s) in the reaction mixture;
the initiation efficiency; and
the reaction time.

11. The method of claim 1, wherein the monomer comprises at least one or a mixture of at least one hydrophilic monomer with at least one hydrophobic monomer.

12. The method of claim 11, wherein the hydrophilic monomer comprises at least one ionic water-soluble monomer, or at least one non-ionic water-soluble monomer, or a mixture of any two or more thereof.

13. The method of claim 1, wherein the monomer comprises (meth)acrylic acid, alkali metal or ammonium salts thereof, (meth)acrylic acid esters, acrylamides, sulphonated acrylamides, mono- or di-N-alkylated acrylamides, vinyl alcohols, N-vinyl pyrrolidone or a mixture of any two or more thereof.

14. The method of claim 13, wherein the monomer comprises 2-acrylamido-2-methylpropane sulphonic acid, or a salt thereof.

15. The method of claim 14, further comprising an acrylic (3-sulphopropyl) ester or a salt thereof.

16. The method of claim 1, wherein the monomer comprises 3-sulphopropyl acrylate, a salt of 3-sulphopropyl acrylate, diacetone acrylamide, N,N-dimethylacrylamide, N-vinyl pyrrolidone, acryloyl morpholine or a mixture of any two or more thereof.

17. The bioadhesive composition of claim 1, wherein the aqueous reaction mixture further includes at least one photoinitiator, at least one plasticiser, at least one humectant (other than water), at least one electrolyte, at least one surfactant, or a mixture of any two or more thereof.

18. The method of claim 17, wherein said plasticizer comprises any of the following either alone or in combination: at least one polyhydric alcohol, at least one ester derived from polyhydric alcohol and at least one polymeric alcohol.

19. The method of claim 17, wherein said plasticizer comprises at least one of glycerol and an ester derived from boric acid and glycerol.

20. The method of claim 17, wherein said the bioadhesive composition comprises from about 15% to about 45%, by weight of the reaction mixture of said plasticizer (other than water).

21. The method of claim 17, wherein said reaction mixture comprises from about 0.1% to about 5%, by weight of the reaction mixture, of said surfactant.

22. The method of claim 17, wherein said surfactant comprises one or bore non ionic surfactants.

23. The method of claim 17, wherein said surfactant comprises one or more anionic surfactants.

24. The method of claim 17, wherein said surfactant comprises one or more cationic surfactants.

25. The method of claim 17, wherein said surfactant comprises at least one propylene oxide/ethylene oxide block copolymer.

26. The method of claim 1, in that the reaction mixture further comprises at least one lipid micellizing polymer.

27. The bioadhesive composition of claim 26, wherein said reaction mixture comprises from about 0.1% to about 5%, by weight of the reaction mixture, of lipid micellising polymer.

28. The method of claim 26 or claim 27, wherein said lipid micellising polymer comprises any of the following either alone or in combination: poly(maleic acid-styrene), poly(maleic acid-butyl vinyl ether), poly(maleic acid-propyl vinyl ether), poly(maleic acid-ethyl vinyl ether) and poly (acrylic acid-ethyl acrylate).

29. The method of claim 26 to 28, wherein said lipid micellising comprises an alternating copolymer of styrene and maleic acid.

30. The method of claim 11, wherein said reaction mixture comprises from about 1% to about 15%, by weight of the reaction mixture, of said hydrophobic monomer, when present.

31. The method of claim 12, wherein said hydrophobic monomer, when present, comprises any of the following either alone or in combination: n-butyl acrylate, n-butyl methacrylate, a hexyl acrylate, iso-octyl acrylate, isodecyl acrylate, ethoxyethyl acrylate terahydrofurfuryl acrylate, vinyl propionate, and vinyl butyrate.

32. The method of claim 11, wherein said hydrophobic monomer, when present, comprises at least one of ethoxy ethyl acrylate or butyl acrylate.

33. The method of claim 11, wherein said reaction mixture from about 3% to about 20%, by weight of the reaction mixture, of said hydrophobic polymer, when present.

34. The method of claim 11, wherein said hydrophobic polymer, when present, comprises any of the following either alone or in combination: vinylacetate dioctyl maleate copolymer or ethylene vinylacetate copolymer.

35. The method of 1, wherein the polymerization is a free radical polymerization.

36. The method of claim 35, wherein the free radical polymerization is performed in the presence of a photoinitiator.

37. The method of claim 36, wherein said photoinitiator comprises 1-hydroxycyclohexyl phenyl ketone, 2-hydroxy-2-propyl phenyl ketone or a mixture thereof.

38. The method of claim 1, wherein said composition provides adhesion on dry skin at no less than 0.5 N/cm.

39. The method of claim 1, when exhibiting a negative rate of change of tan delta against frequency in at least part of the frequency range 0.01 to 100 rad/s.

40. The method of claim 39, when exhibiting a negative rate of change of tan delta against frequency in at least part of the frequency range 0.01 to 30 rad/s.

41. The method of claim 39, when exhibiting water stability as herein defined.

42. The method claim 1, when exhibiting a continuously substantially zero rate of change of tan delta against frequency in at least part of the frequency range 0.01 to 100 rad/s.

43. The method of claim 42, when exhibiting a continuously substantially zero rate of change of tan delta against frequency in at least part of the frequency range 0.01 to 30 rad/s.

44. The method of claim 1, when exhibiting a positive rate of change of tan delta against frequency in at least part of the frequency range 0.01 to 100 rad/s.

45. The method of claim 44, when exhibiting a positive rate of change of tan delta against frequency in at least part of the frequency range 0.01 to 30 rad/s.

46. The method of claim 1, when exhibiting a zero rate of change of tan delta against frequency at only one point in the frequency range 0.01 to 300 rad/s.

47. The method of claim 2, wherein the desired degree of polymerization and/or the degree of cross-linking and/or entanglement in the polymerized composition is achieved by selection of the amount of monomer in the aqueous reaction mixture, the amount of any cross-linking agent present in the aqueous reaction mixture, and/or the reaction conditions for the polymerization with cross-linking and/or entanglement.

48. The method of claim 2, wherein the diagnostic portion of the frequency range is less than about 100 rad/s.

49. The method of claim 48, wherein the diagnostic portion of the frequency range is less than about 30 rad/s.

50. The method of claim 48, wherein the diagnostic portion of the frequency range is less than about 10 rad/s.

51. The method of claim 2, wherein the measurement of elastic modulus and viscous modulus is carried out at a temperature of about 37C.

52. The method of claim 47, wherein a cross-linking agent is present in the aqueous reaction mixture and the relative amount of monomer and cross-linking agent is selected to achieve the desired degree of cross-linking.

53. The method of claim 51, wherein a cross-linking agent is present in aqueous reaction mixture and the molar ratio of monomer(s) to cross-linking agent(s) is selected within the range of about 10,000:1 to about 200:1.

54. The method of claim 47, wherein the reaction conditions for the polymerization with cross-linking and/or entanglement are selected by controlling one or more of the following aspects of the polymerization reaction:

the reactivity of the monomer(s) and the number of polymerizable functions per molecule;

the reactivity of the cross-linking agent(s) and the number of reactive functions per molecule;

the presence of any polymerization inhibitor(s);

the presence of any chain-transfer agent(s);

the weight fraction of monomer(s) and cross-linking agent(s) in the reaction mixture;

the initiation efficiency; and the reaction time.

55. The method of claim 2, wherein the monomer comprises at least one hydrophilic monomer, or a mixture of at least one hydrophilic monomer with at least one hydrophobic monomer.

56. The method of claim 55, wherein the hydrophilic monomer comprises at least one ionic water-soluble monomer, or at least one non-ionic water-soluble monomer, or a mixture of any two or more thereof.

57. The method of claim 2, wherein the monomer comprises (meth)acrylic acid, alkali metal or ammonium salts thereof, (meth)acrylic acid esters, acrylamides, sulphonated acrylamides, mono- or di-N-alkylated acrylamides, vinyl alcohols, N-vinyl pyrrolidone or a mixture of any two or more thereof.

58. The method of claim 57, wherein the monomer comprises 2-acrylamido-2-methylpropane sulphonic acid, or a salt thereof.

59. The method of claim 58, further comprising an acrylic (3-sulphopropyl)ester or a salt thereof.

60. The method of claim 2, wherein the monomer comprises 3-sulphopropyl acrylate, a salt of 3-sulphopropyl acrylate, diacetone acrylamide, N,N-dimethylacrylamide, N-vinyl pyrrolidone, acryloyl morpholine or a mixture of any two or more thereof.

61. The bioadhesive composition of claim 2, wherein the aqueous reaction mixture further includes at least one photoinitiator, at least one plasticiser, at least one humectant (other than water), at least one electrolyte, at least one surfactant, or a mixture of any two or more thereof.

62. The method of claim 61, wherein said plasticizer comprises any of the following either alone or in combination: at least one polyhydric alcohol, at least one ester derived from polyhydric alcohol and at least one polymeric alcohol.

63. The method of claim 61, wherein said plasticizer comprises at least one of glycerol and an ester derived from boric acid and glycerol.

64. The method of claim 61, wherein said the bioadhesive composition comprises from about 15% to about 45%, by weight of the reaction mixture of said plasticizer (other than water).

65. The method of claim 61, wherein said reaction mixture comprises from about 0.1% to about 5%, by weight of the reaction mixture, of said surfactant.

66. The method of claim 61, wherein said surfactant comprises one or more non ionic surfactants.

67. The method of claim 61, wherein said surfactant comprises one or ore anionic surfactants.

68. The method of claim 61, wherein said surfactant comprises one or more cationic surfactants.

69. The method of claim 61, wherein said surfactant comprises at least one propylene oxide/ethylene oxide block copolymer.

70. The method of claim 2, in that the reaction mixture further comprises at least one lipid micellizing polymer.

71. The bioadhesive composition of claim 70, wherein said reaction mixture comprises from about 0.1% to about 5%, by weight of the reaction mixture, of lipid micellising polymer.

72. The method of claim 70 or claim 71, wherein said lipid micellising (polymer comprises any of the following either alone or in combination: poly(maleic acid-styrene), poly(maleic acid-butyl vinyl ether), poly(maleic acid-propyl vinyl ether), poly(maleic acid-ethyl vinyl ether) and poly (acrylic acid-ethyl acrylate).

73. The method of claims 70–72, wherein said lipid micellising polymer comprises an alternating copolymer of styrene and maleic acid.

74. The method of claim 55, wherein said reaction mixture comprises from about 1% to about 15%, by weigh(of the reaction mixture, of said hydrophobic monomer, when present.

75. The method of claim 55, wherein said hydrophobic monomer, when present, comprises any of the following either alone or in combination: n-butyl acrylate, n-butyl methacrylate, a hexyl acrylate, iso-octyl acrylate, isodecyl acrylate, ethoxyethyl acrylate tehrahydrofurfuryl acrylate, vinyl propionate, and vinyl butyrate.

76. The method of claim 55, wherein said hydrophobic monomer, when present, comprises at least one of ethoxy ethyl acrylate or butyl acrylate.

77. The method of claim 55, wherein said reaction mixture from about 3% to about 20%, by weight of the reaction mixture, of said hydrophobic polymer, when present.

78. The method of claim 55, wherein said hydrophobic polymer, when present, comprises any of the following either alone or in combination: vinylacetate dioctyl maleate copolymer or ethylene vinylacetate copolymer.

79. The method of claim 2, wherein the polymerization is a free radical polymerization.

80. The method of claim 79, wherein the free radical polymerization is performed in the presence of a photoinitiator.

81. The method of claim 80, wherein said photoinitiator comprises 1-hydroxycyclohexyl phenyl ketone, 2-hydroxy-2-propyl phenyl ketone or a mixture thereof.

82. The method of claim 2, wherein said composition provides adhesion on dry skin at no less than 0.5 N/cm.

83. The method of claim 2, when exhibiting a negative rate of change of tan delta against frequency in at least part of the frequency range 0.01 to 100 rad/s.

84. The method of claim 83, when exhibiting a negative rate of change of tan delta against frequency in at least part of the frequency range 0.01 to 30 rad/s.

85. The method of claim 83, when exhibiting water stability as herein defined.

86. The method of claim 2, when exhibiting a continuously substantially zero rate of change of tan delta against frequency in at least part of the frequency range 0.01 to 100 rad/s.

87. The method of claim 86, when exhibiting a continuously substantially zero rate of change of tan delta against frequency in at least part of the frequency range 0.01 to 30 rad/s.

88. The method of claim 2, when exhibiting a positive rate of change of tan delta against frequency in at least part of the frequency range 0.01 to 100 rad/s.

89. The method of claim 88, when exhibiting a positive rate of change of tan delta against frequency in at least part of the frequency range 0.01 to 30 rad/s.

90. The method of claim 2, when exhibiting a zero rate of change of tan delta against frequency at only one point in the frequency range 0.01 to 300 rad/s.

* * * * *